United States Patent [19]

Ayral-Kaloustian et al.

[11] Patent Number: 5,312,831
[45] Date of Patent: May 17, 1994

[54] URETHANES AND UREAS THAT INDUCE CYTOKINE PRODUCTION

[75] Inventors: Semiramis Ayral-Kaloustian, Tarrytown; Steven R. Schow, Washingtonville; Mila T. Du, Suffern, all of N.Y.; James J. Gibbons, Jr., Westwood, N.J.

[73] Assignee: American Cyanamid Company, Wayne, N.J.

[21] Appl. No.: 63,174

[22] Filed: May 12, 1993

[51] Int. Cl.$^5$ ...................... A61K 37/00; C07C 261/00
[52] U.S. Cl. ........................................ 514/478; 514/19; 514/484; 514/485; 514/488; 514/489; 514/566; 544/58.4; 544/168; 544/224; 544/237; 544/335; 544/355; 544/383; 544/390; 544/406; 546/146; 546/147; 546/255; 546/262; 546/496; 562/439; 562/560; 564/47; 564/57; 564/59; 548/127; 548/136; 548/200; 548/214; 548/236; 548/248; 548/253; 548/333.5; 548/374.1; 548/495; 548/530; 549/72; 549/365; 549/366; 549/487; 560/25; 560/28; 560/29; 560/32; 560/33; 560/34; 560/115; 560/158; 560/159

[58] Field of Search ...................... 560/159, 25, 28, 29, 560/32, 33, 34, 115, 158; 564/47, 57, 59; 562/560, 439; 544/58.4, 168, 224, 237, 335, 355, 383, 390, 406; 546/146, 147, 255, 262, 496; 548/127, 136, 200, 214, 236, 248, 253, 343, 352, 378, 495, 530; 549/72, 365, 366, 487; 514/566, 19, 478, 484, 485, 488, 489

[56] References Cited

U.S. PATENT DOCUMENTS 4,261,979 4/1981 Jolles et al. .
4,349,466 9/1982 Kitaura et al. .
4,666,890 5/1987 Kitaura et al. .

FOREIGN PATENT DOCUMENTS 2053231 2/1981 United Kingdom .

OTHER PUBLICATIONS

Dezelee et al., Biochemistry, 9: 823-831 (1970) "Stereo-Specific Synthesis of Meso-Diaminopimelic Acid Peptides".
Ellouz et al., Biochem. Biophys. Res. Comm., 59: 1317-1325 (1974), "Minimal Structural Requirements for Adjuvant Activity of Bacterial Peptidoglycan Derivatives".
Kolodziejczyk et al., Int. J. Peptide Protein Res., 39: 382-387 (1992), "New Convenient Synthesis of Immunostimulating Peptides Containing Meso-diaminopimelic acid".
Azuma et al., Int. J. Immunopharmac., 14: 487-496 (1992) "Review: Inducer of Cytokines in vivo: Overview of Field and Romurtide Experience".
Hemmi et al., Tet. Lttrs., 23: 693-696 (1982) "An Efficient Method for Selective Amino Acid Protection of Meso-2,2'-Diaminocarboxylic acid".
Nakamura et al., Agric. Biol. Chem. 48(10): 2579-2580 (1984), "Induction of Colony-stimulating Factor (CSF) by FK-156 and Its Synthetic Derivative, FK-565".
Izumi et al., J. Antibiotics, 36(5): 566-574 (1983), "Antitumor Effects of Novel Immunoactive Peptides".
Nakajima et al., Arzneim. Forsch./Drug Res., 41(I): 60-64 (1991), "Stimulatory Effect of Romurtide on Hematopoiesis in Monkeys".

Primary Examiner—Michael L. Shippen
Attorney, Agent, or Firm—K. J. Dow

[57] ABSTRACT

The invention relates to novel ureas and urethanes of Formula I:

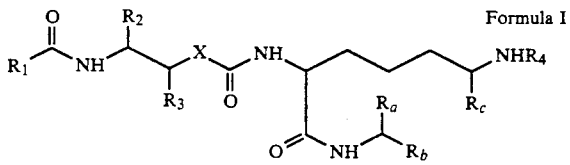

which stimulate cytokine production and may be used to accelerate recovery from neutropenia accompanying radio- or chemotherapy, bone marrow transplantation, or infections. Compounds in the invention or pharmaceutical compositions employing these compounds may be useful in the treatment of cancer, AIDS, aplastic anemia, myelodysplastic syndrome, and infectious diseases, and in the enhancement of immune response.

25 Claims, No Drawings

URETHANES AND UREAS THAT INDUCE CYTOKINE PRODUCTION

BACKGROUND OF THE INVENTION

Cytokines such as G-CSF, M-CSF, GM-CSF (colony stimulating factors) and IL-1, IL-3, IL-6 (interleukins) can stimulate hematopoiesis in diseases associated with bone marrow failure and thus accelerate recovery from neutropenia as reported by Metcalf, D., Science, 529, (1991) and H. G. Klingemann and H. J. Deeg, CIPS, 14, 243, (1989) as well as G. Mortsyn and A. W. Burgess, Cancer Research 48, 5624, (1988). Portions of the natural bacterial cell wall and synthetic lipopeptides that mimic the cell wall have been reported to have immunostimulant properties as described by J. Freund, Adv. Tubercl. Res., 1, 130 (1956); F. Ellouz, A. Adam, R. Ciorbaru and E. Lederer, Biochem. Biophys. Res. Commun., 59, 1317, (1974); V. St. Georgiev, Medicinal Res. Rev, 11, 81, (1991) and I. Azuma, Int. J. Immunopharmac., 14, 487 (1992). More specifically, certain compounds have been identified which appear to induce the formation of CSF and can aid in bone marrow restoration after myelosuppression caused by chemotherapy or radiation. These include compounds such as pimelautide (RP-40639), [as reported by F. Floch'h, J. Bouchaudon, C. Fizames, A. Zerial, G. Dutruc-Rosset and G. H. Werner, CIPS, 763 (1984) and in Patent No. FR-2,482,961, (1981)]; muroctasin (Daiichi Seiyaku Co.) [as reported by I. Azuma, Int. J. Immunopharmac., 14, 487 (1992); R. Nakajima, Y. Yshida, K. Akahane, M. Sekiguchi and Y. Osada, Arzneim.-Forsch., 41, 60, (1991); Scrip, 22, 1655 (1991); and Patent No. EP-135,788, (1985)]; and FK-156 and FK-565 (Fujisawa) [as reported by S. Izumi, K. Nakahara, T. Gotoh, S. Hashimoto, T. Kino, M. Okuhara, H. Aoki, and H. Imanaka, J. Antibiotics, 566, (1983); K. Nakamura, K. Nakahara, H. Aoki, Agric. Biol. Chem., 48, 2579 (1984); H. Keiji, H. Takeno, S. Okada, O. Nakguchi, Y. Kitaura, and M. Hashimoto, Tetrahedron Lett., 23, 693 (1982) and U.S. Pat. Nos. 4,349,466 and 4,666,890].

U.S. Pat. No. 4,666,890 discloses a synthetic tripeptide which has been reported to have activity as an immunomodulator, for use as an antitumor agent rather than as an adjuvant to chemotherapy. The reported cell-wall components and their synthetic analogs are all peptides incorporating a D-glutamic acid (D-Glu) moiety γ-linked to either lysine (Lys) or diaminopi- melic acid (A₂pm), with additional peptide bonds or fatty acyl groups flanking the two ends.

The novel urethanes and ureas disclosed in this invention are the first examples of non-peptide analogs of bacterial cell wall components and lack the D-Glu moiety common to prior art. Furthermore, while previous art has provided no branching on the peptide backbone, this invention includes branched analogs that retain the desired activity when synthesized in a specific configuration, and a method of synthesis for these chiral branched analogs.

SUMMARY OF THE INVENTION

The invention relates to urethanes and ureas of the formula:

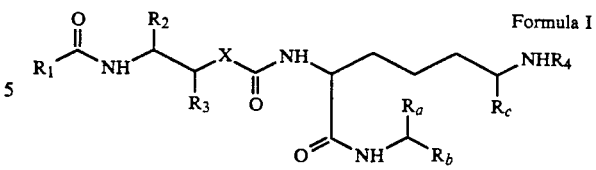

Formula I wherein:
$R_1$ is selected from the group consisting of hydrogen, a substituted or unsubstituted ($C_1$–$C_{20}$) alkyl group, a substituted or unsubstituted cycloalkyl group, a substituted or unsubstituted cycloalkylalkyl group, a vinyl group, an acetylene group, a substituted or unsubstituted amino group, a substituted or unsubstituted acylamino group, a substituted or unsubstituted aryl group, a substituted or unsubstituted aralkyl group, a substituted or unsubstituted aryloxy group, a substituted or unsubstituted alkoxyaryl group, a substituted or unsubstituted alkoxyaralkyl group and a substituted or unsubstituted monocyclic or bicyclic heterocyclic group containing from 1 to 4 hetero atoms selected from the group consisting of nitrogen, sulfur and oxygen atoms; $R_a$ and $R_3$ are independently selected from hydrogen, substituted or unsubstituted ($C_1$–$C_6$) alkyl, substituted or unsubstituted alkoxyalkyl, substituted or unsubstituted cycloalkyl, substituted or unsubstituted cycloalkylalkyl, substituted or unsubstituted aryl, substituted or unsubstituted aralkyl, substituted or unsubstituted alkoxyaralkyl, vinyl, acetylene and a substituted or unsubstituted monocyclic or bicyclic heterocycle containing from 1 to 4 heteroatoms selected from the group consisting of nitrogen, sulfur and n atoms provided that, in the case of R3, the hetero atoms in said heterocycle are not directly bonded to the —CH— group of the —CH—X— moiety; $R_2$, $R_b$ and $R_c$ are independently selected from carboxy or protected carboxy, carboxy or protected carboxyloweralkyl and carboxyamide;

X is oxygen or nitrogen;

$R_4$ is H or an amino protecting group; and the pharmaceutically acceptable salts thereof.

Particulars of the various definitions mentioned above and specific examples falling within such definitions are provided below:

(a) The ($C_1$–$C_{20}$) alkyl group may be a straight chain or branched lower alkyl group having from 1 to 20 carbon atoms such as a methyl group, an ethyl group, a propyl group, an isopropyl group, a butyl group, an isobutyl group, a sec-butyl group, a tert-butyl group, a pentyl group, a neopentyl group, an isopentyl group, a hexyl group, an isohexyl group and so forth.

(b) The cycloalkyl group may be a cycloalkyl group having from 3 to 6 carbon atoms such as a cyclopropyl group, a cyclobutyl group, a cyclopentyl group or a cyclohexyl group.

(c) The cycloalkylalkyl group may be a cycloalkylalkyl group having from 4 to 12 carbon atoms such as a cyclopropylmethyl group, a cyclobutylmethyl group, a cyclopentylmethyl group, a cyclohexylmethyl group, 1-cyclopropylethyl group, a 2-cyclopropylethyl group, a 2-cyclopropylethyl group, a 1-cyclobutylethyl group, a 2-cyclobutylethyl group, a 1-cyclopentylethyl group, a 2-cyclopentylethyl group, a 1-cyclohexylethyl group, a 3-cyclohexylpropyl group, a 3-cyclopentylpropyl group, a 4-cyclohexylbutyl group, a 4-cyclopentylbutyl group, a 4-cyclopentylpentyl group or 4-pentylcyclohexyl group.

(d) The acylamino group may be an acylamino group in which the acyl moiety is derived from an acid such as organic carboxylic acid or carbonic acid, each of which more particularly includes an aliphatic, an aromatic and/or a heterocyclic group in its molecule. These include aliphatic acyl groups having an acyl group derived from an aliphatic acid and includes: alkanoyl (e.g. formyl, acetyl, propionyl, butyryl, isobutyryl, valeryl, isovaleryl, pivaloyl, hexanoyl, α-ethyl-hexanoyl, heptanoyl, lauroyl, stearoyl, docosanoyl, a group of the formula: $CH_3(CH_2)_{31}CO$, $[CH_3(CH_2)_{21}]_2CHCO$, $[CH_3(CH_2)_{15}]_2CHCO$, $CH_3(CH_2)_{41}CO$, etc.); lower alkoxycarbonyl (e.g. methoxycarbonyl, ethoxycarbonyl, propoxycarbonyl, butoxycarbonyl, t-butoxycarbonyl, t-pentoxycarbonyl, etc.) and the like. The acyl moiety may also be an aromatic acyl meaning an acyl group derived from an acid having a substituted or unsubstituted aryl group, in which the aryl group may include phenyl, tolyl, xylyl, naphthyl and the like, and suitable examples thereof are illustrated as follows aroyl (e.g. benzoyl, toluoyl, xyloyl, naphthoyl, phthaloyl, etc.); aralkoxycarbonyl (e.g. benzyloxycarbonyl, benzhydroloxycarbonyl, trityloxycarbonyl, α-naphthylmethoxycarbonyl, etc.) and the like. The acyl moiety may also be a heterocyclic acyl group meaning an acyl group derived from an acid having a heterocyclic group and includes: heterocyclic carbonyl, in which the heterocycle moiety is 5 to 6 membered heterocycle containing at least one to four heteroatoms selected from nitrogen, oxygen and sulfur (e.g. thienoyl, furoyl, pyrrolecarbonyl, 5-oxo-2-pyrrolidinecarbonyl, nicotinoyl, etc.) and the like.

(e) The aryl group may be an aryl group having from 6 to 15 carbon atoms such as a phenyl group, a biphenylyl group, a 1-naphthyl group or a 2-naphthyl group.

(f) The aralkyl group may be an aralkyl group having from 7-15 carbon atoms such as a benzyl group, a 1-naphthylmethyl group, a 2-naphthylmethyl group, a 5,6,7,8-tetrahydro-1-naphthyl group, a 5,6,7,8-tetrahydro-2-naphthyl group, a phenethyl group, a 3-phenylpropyl group or a 4-phenylbutyl group.

(g) The aryloxy group may be an aryloxy group having from 6-15 carbon atoms such as a phenoxy group, a biphenyloxy group, a 1-naphthyloxy group, or a 2-naphthyloxy group.

(h) The alkoxyaryl or alkoxyaralkyl group may be an alkoxyaryl or alkoxyaralkyl group having from 6 to 21 carbon atoms such as a benzoyl group, or an alkoxyphenylmethyl group.

(i) The monocyclic or bicyclic heterocyclic group containing from 1 to 4 hetero atoms selected from the group consisting of nitrogen, sulfur and oxygen atoms, may be a heterocyclic group having from 4-15 carbon atoms such as a pyrrolyl group, a furyl group, a thienyl group, a pyridyl group, an imidazolyl group, a pyrazolyl group, a thiazolyl group, an isothiazolyl group, an isoxazolyl group, an oxazolyl group, a pyrazinyl group, a pyrimidinyl group, a pyridazinyl group, an indolyl group, a quinolyl group, an isoquinolyl group, a phthalazinyl group, a naphthidinyl group, a quinoxalinyl group, a quinazolinyl group, a 1,4-benzodioxanyl group, a 1,3-benzodioxanyl group, a 1,2,3-triazolyl group, a 1,3,4-triazolyl group, a 1,3,4-thiadiazolyl group, a 1,2,3-thiadiazolyl group, a tetrazolyl group, a tetrahydrofuranyl group, a tetrahydrothienyl group, a pyrrolidinyl group, an imidazolidinyl group, a 2-imidazolinyl group, a morpholinyl group, a morpholino group, a piperizine N-oxide group, a piperazine N-oxide group, a morpholine N-oxide group, a lower alkyl morpholino group such as an N-methylmorpholino group, an N-ethylmorpholino group or an N-propylmorpholino group, a piperazinyl group, a piperidino group, a piperidinyl group, a thiomorpholino group or a thiomorpholinyl group.

The substituents in the aforementioned groups (a)–(i) may be a halogen atom such as a chlorine atom, a fluorine atom or a bromine atom, a hydroxyl group; a lower alkyl group such as a methyl group, an ethyl group, a propyl group, an isopropyl group, a butyl group, an isobutyl group, a sec-butyl group or a tert-butyl group; a lower alkoxy group such as a methoxy group, an ethoxy group, a propoxy group, an isopropoxy group, a butoxy group, an isobutoxy group, a sec-butoxy group or a tert-butoxy group; an aryloxy group such as a phenoxy group, a 1-naphthyloxy group or a 2-naphthyloxy group; an aralkyloxy group such as a benzyloxy group, a phenethyloxy group, a 1-naphthylmethyloxy group or a 2-naphthylmethyloxy group; an amino group; a mono- or di-lower alkylamino group such as a methylamino group, an ethylamino group, a propylamino group, an isopropylamino group, a butylamino group, a sec-butylamino group, an isobutylamino group, a tert-butylamino group, a dimethylamino group or a diethylamino group; an arylamino group such as a phenylamino group, a 1-naphthylamino group or a 2-naphthylamino group; an aralkylamino group such as a benzylamino group, a phenethylamino group, a 1-naphthylmethylamino group or a 2-naphthylmethylamino group; a carboxyl group; a formyl group; a lower alkoxycarbonyl group such as a methoxycarbonyl group, an ethoxycarbonyl group, a propoxycarbonyl group, an isopropoxycarbonyl group, a butoxycarbonyl group, a sec-butoxycarbonyl group, an isobutoxycarbonyl group or a tert-butoxycarbonyl group; an aryloxy carbonyl group such as a phenoxycarbonyl group, a 1-naphthyloxycarbonyl group or a 2-naphthyloxycarbonyl group; an aralkyloxycarbonyl group such as a benzyloxycarbonyl group, a phenethyloxycarbonyl group, a 1-naphthylmethyloxycarbonyl group or a 2-naphthylmethyloxycarbonyl group; a mercapto group; a lower alkylthio group such as a methylthio group, an ethylthio group, a propylthio group, an isopropylthio group, a butylthio group, a sec-butylthio group, an isobutylthio group or a tert-butylthio group; an arylthio group such as a phenylthio group, a 1-naphthylthio group or a 2-naphthylthio group; an aralkylthio group such as a benzylthio group, a phenethylthio group, a 1-naphthylmethylthio group or a 2-naphthylmethylthio group; an arylsulfinyl group such as a phenylsulfinyl group, a 1-naphthylsulfinyl group or a 2-naphthylmethylthio group; an arylsulfinyl group such as a phenylsulfinyl group, a 1-naphthylsulfinyl group or a 2-naphthylsulfinyl group; an aralkylsulfinyl group such as a benzylsulfinyl group, a phenethylsulfinyl group, a 1-naphthylmethylsulfinyl group or a 2-naphthylmethylsulfinyl group; a lower alkylsulfonyl group such as a mesylgroup, an ethylsulfonyl group, a propylsulfonyl group, an isopropylsulfonyl group, a butylsulfonyl group, an isobutylsulfonyl group, a sec-butylsulfonyl group or a tert-butylsulfonyl group; an arylsulfonyl group such as a phenylsulfonyl group, a 1-naphthysulfonyl group or a 2-naphthylsulfonyl group; an aralkylsulfonyl group such as a benzylsulfonyl group, a phenethylsulfonyl group, a 1-naphthylmethylsulfonyl group or a 2-naphthylmethylsulfonyl group; or a monocyclic or bicyclic heterocyclic group having 4–15 carbon atoms and 1–4 hetero atoms selected from oxygen, nitrogen and sulfur such as a pyrrolyl group, a furyl group, a thienyl group, a pyridyl group, an imidazolyl group, a pyrazolyl group, a thiazolyl group, an isothiazolyl group, an isoxazolyl group, an oxazolyl group, a pyrazinyl group, a pyrimidinyl group, a pyridazinyl group, an indolyl group, a quinolyl group, an isoquinolyl group, a phthalazinyl group, a naphthidinyl group, a quinoxalinyl group, a quinazolinyl group, a 1,4-benzodioxanyl group, a 1,3-benzodioxanyl group, a 1,2,3-triazolyl group, a 1,3,4-triazolyl group, a 1,3,4-thiadiazolyl group, a 1,2,3-thiadiazolyl group, a tetrazolyl group, a tetrahydrofuranyl group, a tetrahydrothienyl group, a pyrrolidinyl group, an imidazolidinyl group, a 2-imidazolinyl group, a morpholinyl group, a morpholino group, a morpholine N-oxide group, a lower alkyl morpholino group such as an N-methylmorpholino group, an N-ethylmorpholino group or an N-propylmorpholino group, a piperazinyl group, a piperidino group, a piperidinyl group, a thiomorpholino group or a thiomorpholinyl group.

As used herein, "lower alkyl" means a C1–C6 alkyl group.

A protecting group for the protected carboxy or protected carboxyloweralkyl include any conventional protecting groups for carboxy groups as routinely used by those skilled in the art of peptide and amino acid chemistry such as those found in T. Greene, "Protecting Groups in Organic Synthesis", J. Wiley and Sons, 1981. These include silyl esters, aliphatic esters, and aromatic esters such as trimethylsilyl, t-butyldimethylsilyl, acetyl, benzoyl, and the like.

A protecting group for the protected amino group includes any conventional protecting group for amino groups as routinely used by those skilled in the art of peptide and amino acid chemistry such as those found in T. Greene, supra. pp.218–287. A suitable protecting group is chosen such that conditions for its removal are compatible with other structural features of the compound. Suitable protecting groups include acyl groups such as tert-butoxycarbonyl or benzyloxycarbonyl and the like.

DETAILED DESCRIPTION OF THE INVENTION

Relative to the above generic description, compounds of Formula I which are preferred are those in which:

$R_1$ is selected from the group consisting of a substituted or unsubstituted ($C_1$–C alkyl group, a substituted or unsubstituted cycloalkyl group, a substituted or unsubstituted cycloalkylalkyl group, a substituted or unsubstituted aryl group, a substituted or unsubstituted aralkyl group, a substituted or unsubstituted aryloxy group, a substituted or unsubstituted alkoxyaryl group, and a substituted or unsubstituted alkoxyaralkyl group wherein the aryl moiety in the foregoing groups is selected from substituted or unsubstituted phenyl;

$R_a$ and $R_3$ are independently selected from hydrogen, and substituted or unsubstituted ($C_1$–$C_6$) alkyl;

$R_2$, $R_b$ and $R_c$ are independently selected from carboxy or protected carboxy, carboxy or protected carboxyloweralkyl and carboxyamide;

X is oxygen or nitrogen; and $R_4$ is H or an amino protecting group.

Furthermore, most preferred compounds of Formula I according to the present invention are those of Formula I in which:

$R_1$ is selected from the group consisting of a ($C_4$–$C_{14}$) alkyl group, a cycloalkyl group, a ($C_2$–$C_8$) alkyl substituted cycloalkyl group, a phenyl group, a benzyl group, a ($C_4$–$C_8$) alkylphenyl group, and a ($C_1$–$C_6$) alkyl or alkoxyphenylmethyl group;

$R_a$ and $R_3$ are independently selected from hydrogen, and ($C_1$–$C_6$) alkyl;

$R_2$, $R_b$ and $R_c$ are independently selected from carboxy or protected carboxy, carboxy or protected carboxyloweralkyl and carboxyamide;

X is oxygen or nitrogen; and $R_4$ is H or an amino protecting group.

Compounds of the Formula I which are most particularly preferred are those in which:

$R_1$ is selected from the group consisting of an n-hexyl group, a 4-n-pentyl cyclohexyl group;

$R_a$ and $R_3$ are independently selected from hydrogen or methyl;

$R_2$, $R_b$ and $R_c$ are carboxy;

X is oxygen or nitrogen; and $R_4$ is H.

Particularly preferred are those compounds of Formula I having the D-allo-threonine configuration as follows:

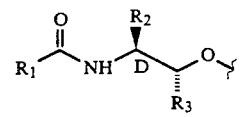

wherein $R_3$ is methyl, and $R_1$ and $R_2$ are hereinbefore defined.

Also particularly preferred are those compounds having the following stereochemistry in the diaminopimelyl-alanine portion of the molecule:

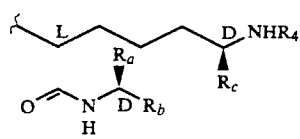

wherein $R_a$ is methyl, and $R_b$, $R_c$ and $R_4$ are as hereinbefore defined.

With respect to stereochemistry, the following compounds of Formula I are most particularly preferred:

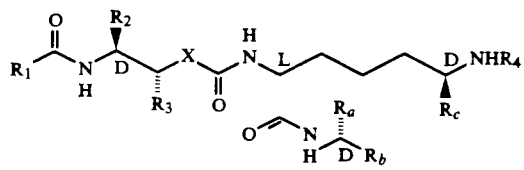

wherein $R_3$ and $R_a$ are methyl, X is oxygen, $R_b$, $R_c$, $R_1$, $R_2$, $R_4$ are hereinbefore defined.

The urethane and ureas of type 1 that are the subject of this invention are constructed by a convergent synthesis, outlined below.

Scheme II

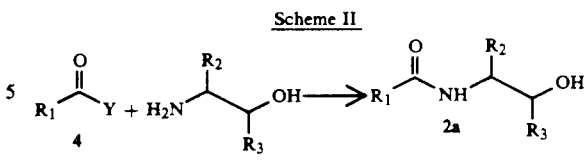

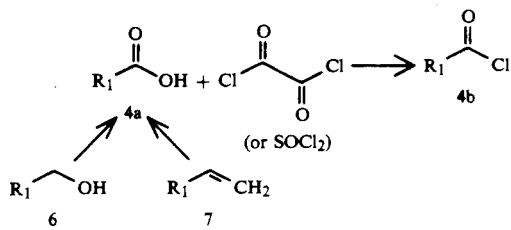

Scheme I

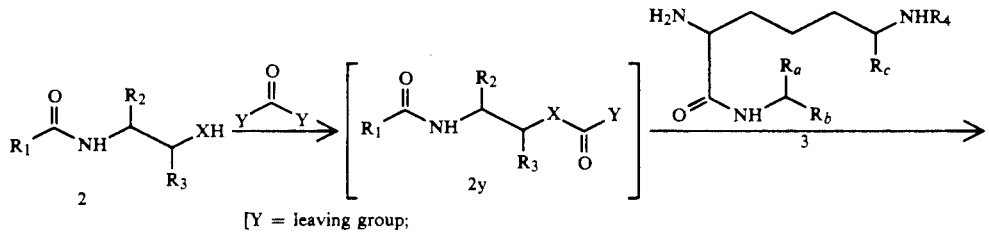

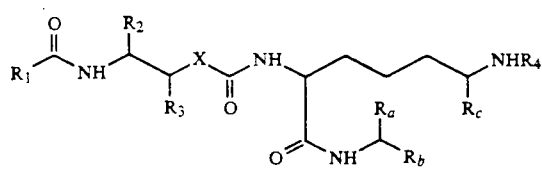

The left-hand (X=O, alcohol 2b, or X=NH, amine 2c) and right-hand (amine 3) fragments, bearing suitable protective groups (examples of commonly used amine protecting groups are found in T. Green, "Protecting Groups in Organic Synthesis," J. Wiley and Sons, 1981, pp 218-287) on the multiple functional groups, are prepared separately. Compound 2 is first made to react with an activated carbonyl equivalent, YC(=O)Y, such as phosgene, triphosgene, phosgene/pyridine adduct, trichlormethyl chloroformate, or 1,1'-carbonyldiimidazole, usually at 0° C. and the ersulting intermediate 2y is coupled with 3 to provide the urethane 1a (X=O) or urea 1b (X=NH), respectively. Alternately, amine 3 is first made to react with YC(=O)Y and the resulting intermediate is coupled with 2 to provide 1a or 1b. Wherever applicable, protective groups are removed under standard conditions to get compounds of type 1 with unmasked functionalities.

Left-hand fragments: For the synthesis of the left-hand fragment 2a, the selective N-acylation of amino alcohols 5 is achieved using a suitable acylating agent 4, under basic conditions. If not available, the desired acylating agent is made from the corresponding acid 4a, which in turn can be made by oxidation of 6 or oxidative degradation of 2c-1 by conventional methods.

Compounds 2c (2a, where $R_2=CO_2H$) are converted to the ester 2e or amide 2f under acidic conditions, using a suitable alcohol (R"OH) or amine (R"NH$_2$), respectively. Alternately, 2c is esterified using an alkylating agent R"Y under basic conditions.

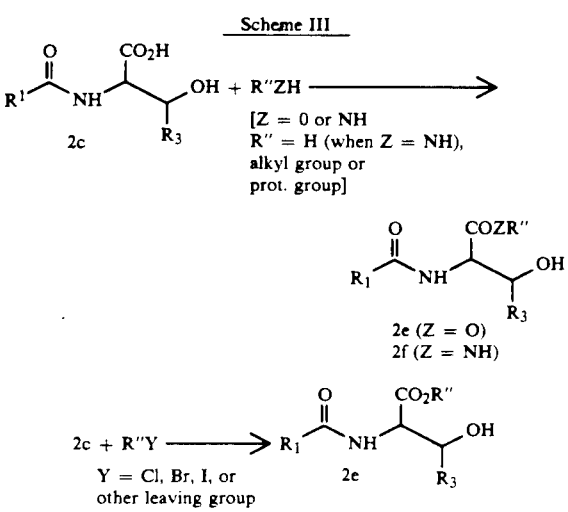

Alcohols 2c with varied $R_3$ alkyl branches are prepared according to Scheme IV. Alcohol 2j is masked with a suitable protecting group (while the NH remains free, is protected as a cyclic N,O-acetal together with the OH, or is blocked with a separate amine protective group) and the ester 8 is reduced to the aldehyde 9 in one step (Garner and Park, J. Org. Chem., 1987, 52, 2361) or two steps via reduction to alcohol and reoxidation, using conventional methods. Addition of suitable organometallic reagents $R_3M$ to the aldehyde provides 10 as a single diastereomer or a mixture of two diastereomers, provided the starting material 2j is not racemic. Unmasking of the primary alcohol (and NH, if blocked) to get 11, followed by selective oxidation (according to Skarzewski, et. al., Tetrahedron Lett., 1990, 31, 2177,) followed by standard oxidation of the resulting aldehyde (according to Mehltretter, et. al., J. Amer. Chem. Soc., 1950, 73, 2424) yields 2c. Alternately, the secondary alcohol in 10 is protected and the primary alcohol (and NH, if blocked) in the resulting 12 is unmasked selectively to provide 13. Using conventional techniques, the latter is oxidized to 14 which is converted to 2c. The primary and secondary alcohol functionalities in 11 are also protected sequentially to provide 12 (W=H). The net transformation from 2j to 2c involves an inversion of the configuration at the carbon α to the carboxyl group, by transposition of the carboxyl and alcohol moieties, and the introduction of an $R_3$ group at the β position, with chirality. Diastereomers of 10, 12 or 13 may be separated by chromatography. Thus, 2j of R configuration at the α position can provide 2c diastereomers of S,R (α,β) and S,S (α,β) configuration and 2j of S configuration can provide 2c diastereomers of R,R (α,β) and R,S (α,β) configuration.

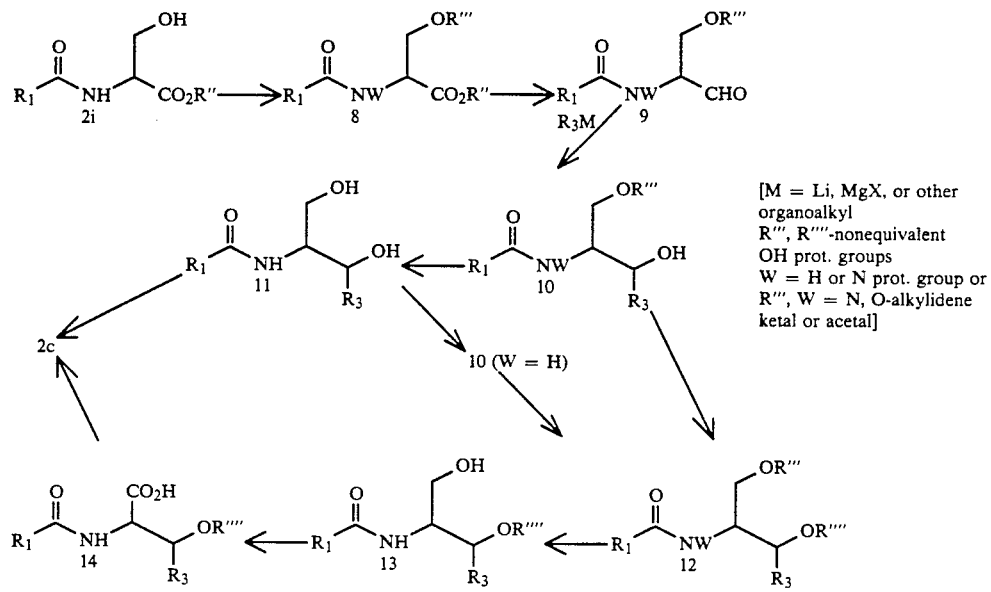

Scheme IV

[M = Li, MgX, or other organoalkyl
R''', R''''-nonequivalent OH prot. groups
W = H or N prot. group or R''', W = N, O-alkylidene ketal or acetal]

Alternately, 11 or 12 can be prepared from 5j according to Scheme V. The amine is fully blocked with two protective groups or a cyclic protective group to get 15. Conversion 15 to 16 to 17 to 19 is the same reaction sequence described for 8 to 9 to 10 to 12, above. The amine protective groups in 17 or 19 are removed to provide 18 or 20, respectively. The latter are acylated to get 11 or 12.

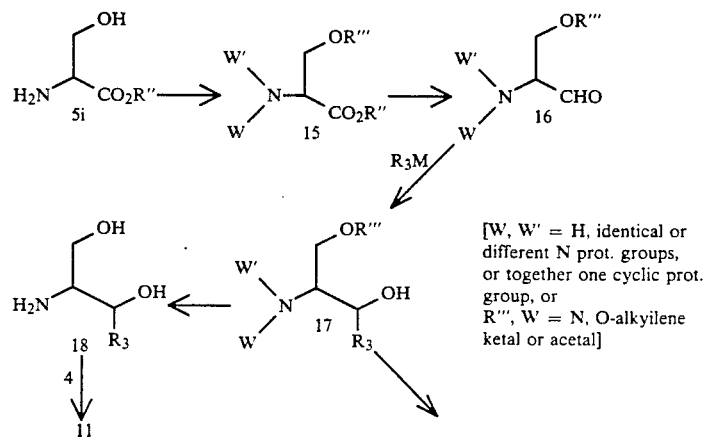

Scheme V

[W, W' = H, identical or different N prot. groups, or together one cyclic prot. group, or
R''', W = N, O-alkyilene ketal or acetal]

Scheme V

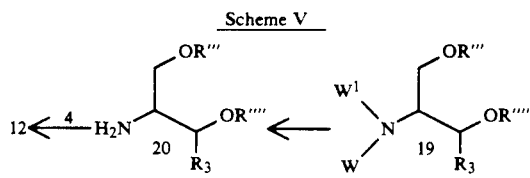

For the synthesis of the left-hand fragment 2b, the acylation of amine 21 under basic conditions provides 22. The primary amide is rearranged to the amine 2b (according to Loudon, et. al., J. Org. Chem., 1984, 49, 4272; Waki, et. al., Synthesis, 1981, 53, 266; or Koser, et. al., J. Org. Chem., 1988, 53, 5158).

Scheme VI

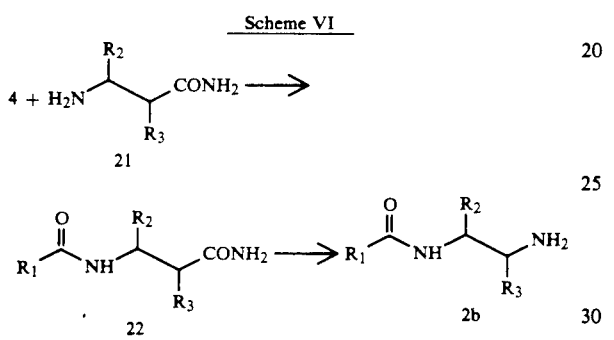

Compounds 2g (2b, where $R_2=CO_2H$) are converted to the ester 2h or amide 2i (shown in Scheme VII) under acidic conditions, using a suitable alcohol (R"OH) or amine (R"NH$_2$), respectively. Alternately, amine 2g is protected as a urethane such as BOC or CBZ; the acid is converted to the ester or amide under basic conditions; and the protective group is removed to get 2h or 2i.

Scheme VII

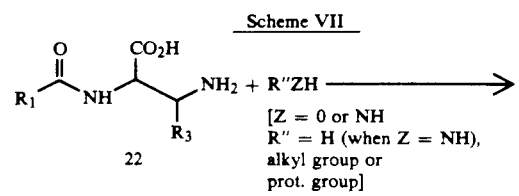

[Z = O or NH
R" = H (when Z = NH),
alkyl group or
prot. group]

2h (Z = O)
2i (Z = NH)

Amines 2g, with varied $R_3$ alkyl branches are prepared according to Scheme VIII. Alcohol 10 is obtained according to Scheme IV, or by reduction of an available acid 2c, followed by protection of the resulting primary alcohol 11. Compound 10 is then converted, by conventional methods, to azide 24 via intermediate 23. The azide moiety is reduced to an amine (25) by catalytic hydrogenation, and the latter masked to get 26. Alternately, standard oxidation of 10 yields 27. Reductive amination of the ketone with a suitable amine (W'''NH$_2$) provides 28, which in turn is converted to 26 (W'''=alkyl, W,,=alkoxycarbonyl), by further protection as a carbamate or to 26 (W"=alkoxycarbonyl, W'''=H) by deprotection (to 25) and reprotection. Unmasking of the primary alcohol in 26 (and amide NH, if blocked) to get 29, followed by oxidation yields 30, as in Scheme IV for conversion of 13 to 14. The amine protective group(s) is(are) removed to yield 2g. Diastereomers carried through from 10 or 28 may be separated by chromatography at one of the intermediate (28, 26, or 29) stages.

Scheme VIII

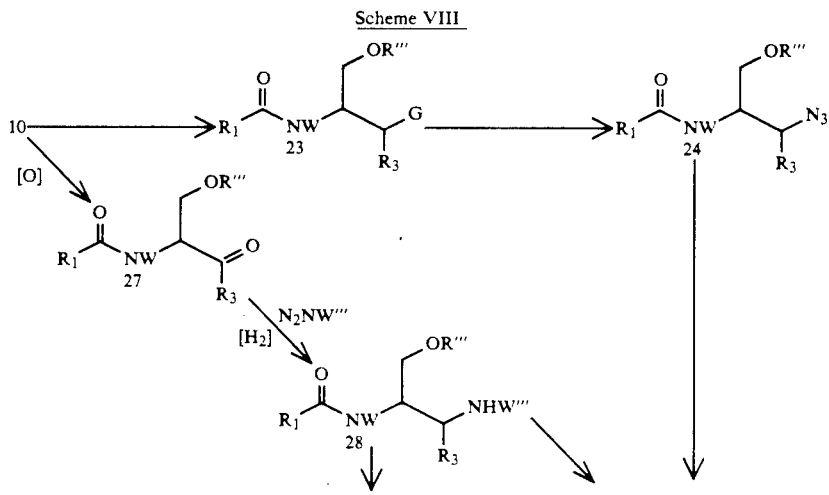

-continued

Scheme VIII

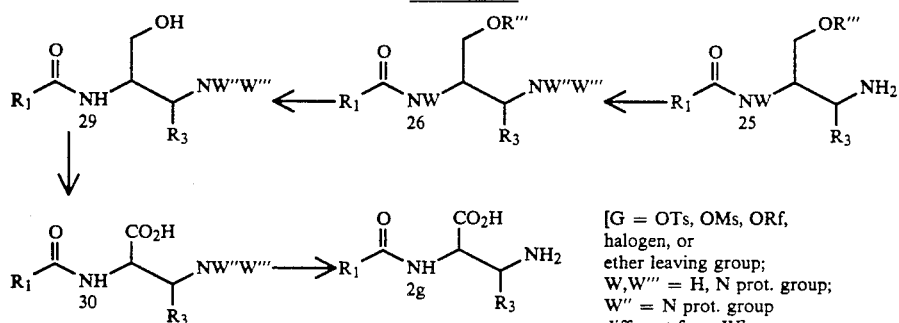

[G = OTs, OMs, ORf, halogen, or ether leaving group;
W,W''' = H, N prot. group;
W'' = N prot. group different from W]

Alternately, 26 can be prepared from 17 according to Scheme IX. Conversions 17 to 31 to 32 to 33 to 34, or 17 to 35 to 36 to 34 are the same reaction sequences as described above for 10 to 23 to 24 to 25 to 26, or 10 to 27 to 28 to 26, respectively. The amine protective groups W and W, are removed to yield 37. The latter is acylated to get 26.

Scheme X

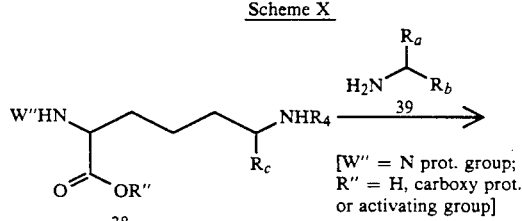

[W'' = N prot. group;
R'' = H, carboxy prot. or activating group]

Scheme IX

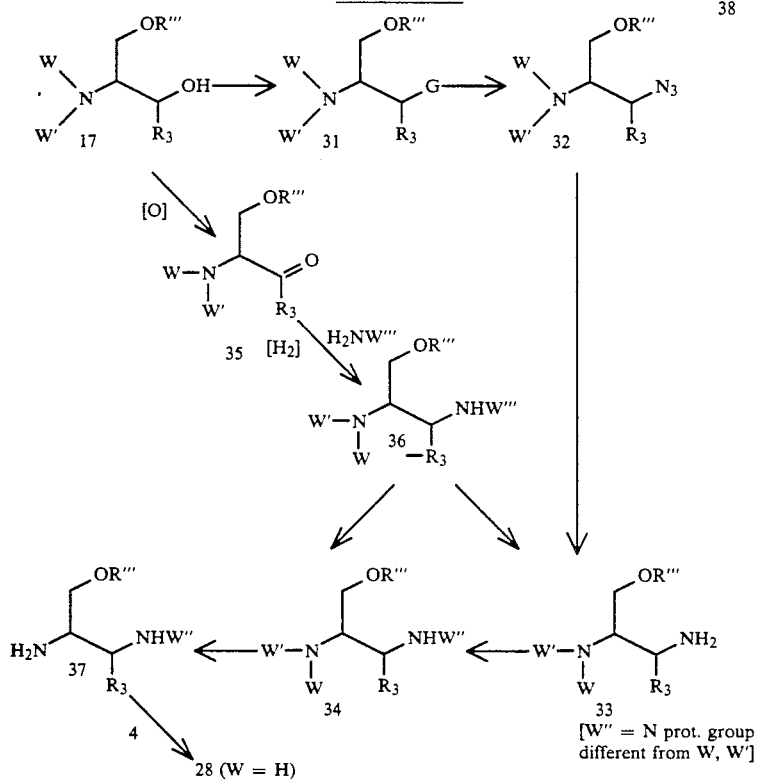

[W'' = N prot. group different from W, W']

Right-hand fragments: Fragment 3 is prepared by coupling of acid (or protected acid) 38 with a suitable amine 39, followed by selective deprotection of the intermediate compound 40.

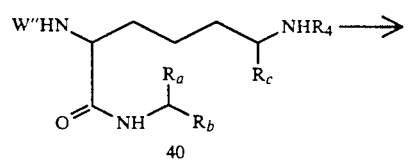

-continued
Scheme X

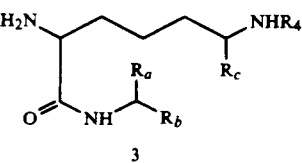

Acids 38 or amides 40 are prepared according to Kolodziejczyk, et. al. (Int. J. Pept. Prot. Res., 1992, 39, 382; and references therein), Jurgens (Tetrahedron Lett., 1992, 33, 4727; and references therein), Williams (J. Org. Chem., 1992, 33, 4727; and references therein), Hashimoto (Tetrahedron Lett., 1982, 23, 693; and references therein), or according to Scheme XI. Glutamic acid (41, chiral or racemic) is protected, under standard conditions, to get 42, which in turn is condensed with formaldehyde to provide 43. The latter is reduced to aldehyde 44 in a one-pot procedure. Wittig-Horner-Emmons type condensation of the aldehyde with a reagent of type 45 (prepared according to Schmidt, et. al., Synthesis, 1984, 53) yields 46. Reaction of the lactone with a suitable amine, 39 (where not available, prepared according to methods outlined in "Synthesis of Optically Active a-Amino Acids", R. M. Williams, Ed., Pergamon Press, 1989; and references therein), with concomitant loss of formaldehyde, provides 47. Catalytic hydrogenation of the double bond yields 40. When ciral 41 is used as the starting material, diastereomers of 40 are separated by fractional crystallization or chromatography. The ratios of diastereomers obtained depends on the choice of protective groups, hydrogenation catalyst, and reaction conditions [Knowles, et. al., J. Amer. Chem. Soc., 99, 5947 (1977); Ojima and Suzuki, Tetrahedron Lett., 21, 1239 (1980)]. Thus, 41 of S configuration gives diastereomers of 40 bearing S,S and S,R configuration on the A$_2$pm and 41 of R configuration can provide diastereomers of 40 bearing R,S and R,R configuration on the A$_2$pm.

The reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically acceptable salts include both the metallic (inorganic) salts and organic salts; a list of which is given in *Remington's Pharmaceutical Sciences*, 17th Edition, pg. 1418 (1985). It is Well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

Some of the compounds of the hereinbefore described schemes have centers of asymmetry. The present invention encompasses all stereoisomers of the compounds whether free from other stereoisomers or admixed with other stereoisomers in any proportion and thus includes, for instance, racemic mixture of enantiomers as well as the diastereomeric mixture of isomers.

The novel compounds of this invention are useful for their ability to induce cytokine formation and restore bone marrow after chemotherapy, as shown by the following tests.

Description of Biological Assays Interleukin 6(IL-6) assay for structure function analysis—Test compounds are dissolved in water and administered subcutaneously in 0.2 ml to deliver a dose of 0.1-10 mg/kg. The less soluble compounds are first dissolved in 100% ethanol and then brought to the appropriate concentration in water. Four hours post injection, the mice are bled and the serum is retrieved. The IL-6 dependent cell line Scheme XI

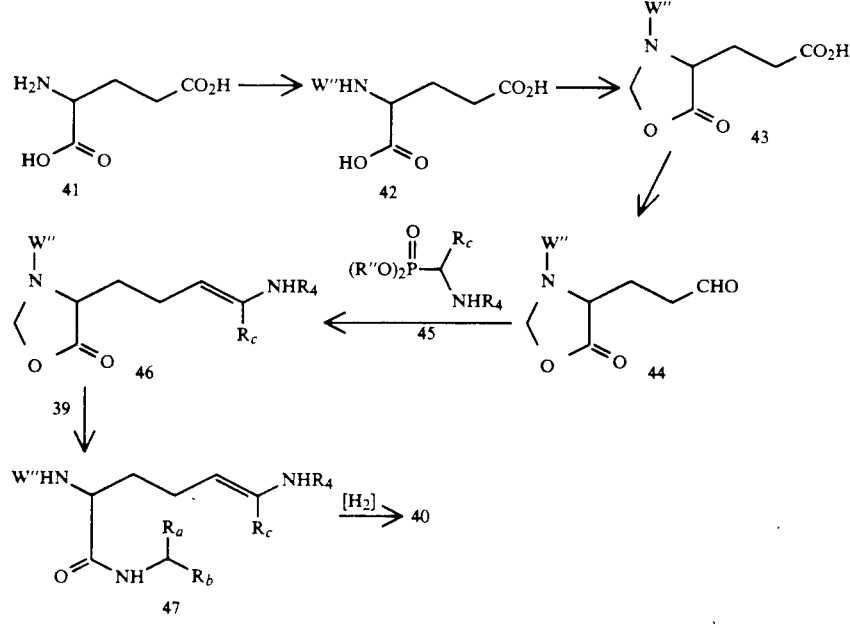

7TD1 is used to assay serial dilutions of sera for IL-6 content. 7TD1 cells ($1 \times 10^4$) are placed in microtiter wells and incubated at 37° C. for 72 hours with standard recombinant mouse IL-6 or with dilutions of serum to be tested. Over the last 6 hours, the cells are pulsed with $^3$H-Tdr ($\mu$ci). Cells are then harvested and the degree of proliferation determined by the uptake of $^3$H-Tdr as measured by liquid scintillation spectrometry. The concentration of IL-6 in serum is calculated from standard curves utilizing recombinant IL-6 from R&D Systems Inc. and are reported in units of IL-6 activity as defined by the manufacturer.

Granulocyte colony stimulating factor (GCSF) assay—A bioassay for GCSF is performed in an identical fashion to the IL-6 assay except that the GCSF dependent cell line NFS-60 is used in place of the IL-6 dependent 7TDI cell line. Neutralizing monoclonal antibody to mouse GCSF is used to prove specificity of the assay.

Colony forming assays Granulocyte-Macrophage (CFU-GM)—Mice are treated with 150 mg/kg of 5-Fu and treatment with test compound begins 24 hrs. later. On consecutive days, mice are killed by cervical dislocation and the femurs removed under sterile conditions. Femurs are flushed with 1 ml of ice cold medium (Iscove's supplemented with 20% FCS, 1% penicillin-streptomycin, 1% glutamine and $5 \times 10^{-5}$ M 2-mercaptoethanol). Bone marrow cells ($5 \times 10^5$) are then plated in $12 \times 75$ mm tissue culture plates in 3 ml of warm ararose (3%) in Iscove's medium with 100 Units/ml of recombinant mouse GM-CSF purchased from Genzyme (Boston, Mass.). Plates are incubated for 7 days at 37° C. in 5% $CO_2$. After 7 days, colonies of 50 cells or greater are enumerated under a dissecting microscope.

Serum colony stimulating factor (CSF) assay—An assay which detects colony stimulating factor activity but does not distinguish between different types of colony stimulating factors is used to detect the presence of CSF activity in the serum of mice injected with test compounds. Bone marrow cells are prepared as described above for the CFU-GM assay. The cells are then incubated in soft agar with an 0.3% final concentration of serum taken from mice 4 hours after injection with test compounds. After 7 days of incubation at 37° C., the number of colony forming (CFU) cells per $10^5$ plated bone marrow cells is determined by counting colonies of more than 50 cells under a dissecting microscope. The data are reported as CFU/$10^5$ bone marrow cells.

Circulating Neutrophil Assay—Mice are treated with 5-FU (150 mg/kg) and beginning 24 hrs. later, treated daily with the test compound. Mice are bled daily by retroorbital puncture in heparinized capillary tubes. Circulating WBC counts are determined by Coulter counter. Blood smears are stained with Wright-Geimsa solution and the percentage circulating neutrophils determined by differential counting under a microscope.

5-Fluorouracil (5-FU) Induced Neutropenia In Mice—Mice are treated ip with 150 mg/kg of the chemotherapy agent 5-FU which induces a severe loss of neutrophils in the peripheral blood 5-6 days later. Twenty-four hrs. after the dose, treatment with the test compounds is initiated. The effect of the test compounds on recovery of neutrophil progenitor cells in the bone marrow is determined by the CFU-GM assay. The recovery of circulating neutrophils is followed by differential staining of the peripheral blood.

Delta Assay—Mice are treated with a single dose of 5-FU (150 mg/kg ip). Twenty-four hours later, bone marrow cells are removed and split into 2 aliquots. One aliquot is plated immediately in soft agar with 15 ng/ml of IL-1 and 250 U/ml GM-CSF. After 14 days, the number of colonies is determined (CFU-1). A second aliquot of cells is placed in liquid culture with single growth factors or drugs or combinations of each to assess the ability of these agents to expand the colony forming cell pool. After 7 days in liquid culture, these cells are harvested and plated in soft agar with IL-1 and GM-CSF as with the first aliquot. After 14 days the number of colonies in the second aliquot is determined (CFU-2). The ratio or delta is calculated as CFU-2/CFU-1 and this ratio is used to ascertain the ability of the growth factors and/or drugs used in the liquid phase to induce growth of the colony forming cells (CFU) or differentiation of pre-CFU to CFU.

Results—Test compounds are able to induce IL-6 production in the serum of mice within 4 hours of a single subcutaneous injection (Table 1). Likewise, serum CSF activity is also detected with these compounds in mice (Table 2). The IL-6 assay is performed in a quantitative fashion and is used to determine relative potency. The CSF assay is performed at a single serum concentration and is therefore qualitative in nature.

A representative compound (Example 28) is shown to also induce GCSF in the serum of injected mice (Table 3). Representative compounds (Examples 28, 32 and 84) are shown to induce neutrophil recovery in 5-FU treated mice (Table 4). A representative compound (Example 28) enhances the recovery of peripheral blood neutrophils which is preceded by an increase of CFU-GM, the neutrophil precursors in the bone marrow (Table 5) thus showing that the test compounds exert an effect in the bone marrow.

A representative compound (Example 28) also induces IL-6 and GCSF production in the serum of 5-FU treated primates (Table 6). A representative compound (Example 32) accelerates the recovery of neutrophils in primates treated with the chemotherapeutic agent cytoxan (Table 7). Test compound treated groups recover to control levels by day 7 versus a day 10 recovery for the cytoxan only group. Thus, the test compounds induce a similar spectrum of cytokines and enhanced neutrophil recovery in both primates and mice.

A representative compound (Example 28) acts synergistically in vitro with the hemopoietic growth factor c-kit ligand (KL) to enhance the growth of bone marrow progenitor cells (Table 8). This further supports the claim that these compounds act to enhance the growth of neutrophil progenitor cells in the bone marrow. The test compounds are also active in accelerating neutrophil recovery in 5-FU treated mice when given orally (Table 9) as shown by a representative compounds (Examples 28 and 32).

Clinical Significance—The data compiled on the test compounds described show that they are able to induce the endogenous production of growth factors (IL-6 and GCSF) which are known to regulate neutrophil production in the bone marrow. These compounds may be used therapeutically to restore neutrophils after cancer chemotherapy, radiation therapy, bone marrow transplantation or infections. In addition, the compounds can be used in combination with recombinant growth factors to potentiate the activity of the recombinant molecules. Also, these compounds may be useful in the treatment of cancer, AIDS, aplastic anemia, myelodysplastic syndrome, infectious diseases and the enhancement of immune response. Unlike recombinant growth factors, the test compounds are effective when given orally.

TABLE 1

Effect of Test Compounds on IL-6 Production in Mice

| Example Number | Dose (mg/kg) | IL-6(U/ml) |
|---|---|---|
| 28 | 10.0 | 1718 |
|  | 1.0 | 3844 ± 482 |
|  | 0.1 | 4802 ± 804 |
| 29 | 10.0 | 537 |
|  | 1.0 | 203 |
|  | 0.1 | 0 |
| 30 | 10.0 | — |
|  | 1.0 | — |
|  | 0.1 | 328 ± 107 |
| 31 | 10.0 | — |
|  | 1.0 | — |
|  | 0.1 | 294 ± 24 |
| 32 | 10.0 | |
|  | 1.0 | 1797 ± 284 |
|  | 0.1 | 1340 ± 134 |
| 33 | 10.0 | |
|  | 1.0 | 3767 ± 457 |
|  | 0.1 | 1651 ± 100 |
| 34 | 10.0 | |
|  | 1.0 | 5063 ± 302 |
|  | 0.1 | 3610 ± 347 |
| 80 | 10.0 | 3624 ± 611 |
|  | 1.0 | 1712 ± 168 |
|  | 0.1 | — |
| 81 | 10.0 | 199 ± 23 |
|  | 1.0 | 56 ± 19 |
|  | 0.1 | — |
| 82 | 10.0 | 3188 ± 345 |
|  | 1.0 | 2181 ± 92 |
|  | 0.1 | |
| 83 | 10.0 | 1818 ± 243 |
|  | 1.0 | 332 ± 38 |
|  | 0.1 | |
| 84 | 10.0 | 2512 ± 209 |
|  | 1.0 | 3865 ± 688 |
|  | 0.1 | 1963 ± 97 |

TABLE 2

Effect of Test Compounds on CSF Production in Mice

| Example Number | Dose (mg/kg) | CFU/100,000 Bone Marrow Cells |
|---|---|---|
| 28 | 10.0 | |
|  | 1.0 | 101 ± 8 |
|  | 0.1 | 95 ± 16 |
| 29 | 10.0 | |
|  | 1.0 | 101 ± 46 |
|  | 0.1 | 0 ± 0 |
| 32 | 10.0 | |
|  | 1.0 | 137 ± 15 |
|  | 0.1 | 154 ± 5 |
| 80 | 10.0 | 121 ± 9 |
|  | 1.0 | 91 ± 3 |
|  | 0.1 | |
| 81 | 10.0 | 101 ± 7 |
|  | 1.0 | 69 ± 14 |
|  | 0.1 | |
| 82 | 10.0 | 115 ± 3 |
|  | 1.0 | 108 ± 11 |
|  | 0.1 | |
| 83 | 10.0 | 123 ± 22 |
|  | 1.0 | 204 ± 9 |
|  | 0.1 | |
| 84 | 10.0 | 131 ± 10 |
|  | 1.0 | 118 ± 15 |
|  | 0.1 | 129 ± 14 |

TABLE 3

Effect of Test Compounds on GCSF Production in Mice

| Example Number | Dose μg/kg | GCSF (pg/ml) |
|---|---|---|
| 28 | 50.00 | 1249 ± 138 |
|  | 25.00 | 3352 ± 907 |
|  | 12.50 | 1342 ± 289 |
|  | 6.25 | 644 ± 267 |
|  | 3.12 | 470 ± 59 |
|  | 1.56 | 442 ± 52 |
|  | 0.00 | 0.00 ± 0 |

Mice (10/group) are given a single subcutaneous injection of test compound and bled 4 hours later. GCSF levels in serum are determined by bioassay using the GCSF dependent cell line NFS-60.

TABLE 4

Effect of Test Compounds on Neutrophil Recovery in 5-FU Treated Mice

| Example Number | μg/kg | *Neutrophils/cu. mm. |
|---|---|---|
| 28 | 100.00 | 2613 ± 364 |
|  | 50.00 | 1716 ± 284 |
|  | 25.00 | 1804 ± 408 |
|  | 12.50 | 1314 ± 267 |
|  | 6.25 | 758 ± 249 |
|  | 3.12 | 424 ± 115 |
|  | 1.56 | 722 ± 199 |
|  | 0.00 | **157 ± 52 |
| ***32 | 1000 | 1892 ± 293 |
|  | 100 | 982 ± 150 |
|  | 0 | 144 ± 36 |
| ****84 | 100 | 2194 ± 629 |
|  | 10 | 570 ± 224 |
|  | 1 | 427 ± 211 |
|  | 0 | 54 ± 22 |

*Data from 10 mice/group on day 7 post treatment with 150 mg/kg of 5-FU. Beginning 24 hrs. after 5-FU dose, mice were treated daily with test compound at concentrations indicated. Neutrophil count for normal mice (n = 5) is 3236 ± 301.
**Mice treated with 5-FU and vehicle only.
***Day 8 post 5-FU
****n = 6 mice/group

TABLE 5

Effect of Test Compounds on Bone Marrow CFU-GM in 5-FU Treated Mice

| Example Number | Group | CFU-GM/femur |
|---|---|---|
| 28 | Normal Mice | 30184 ± 3677 |
|  | 5-FU treated | 805 ± 512 |
|  | 5-FU + Example 28 | 6055 ± 534 |

Groups of 5 mice are treated with 5-FU at 150 mg/kg and beginning 24 hours later treated with test compound daily s.c. at 0.1 mg/kg. The data reported are from day 3 after 5-FU treatment.

TABLE 6

Effect of Test Compounds on Serum IL-6 and GCSF in 5-FU Treated Monkeys

| Example No. | Group | IL-6(Units/ml) | GCSF(pg/ml) |
|---|---|---|---|
| 28 | Normal Monkey | 0 | 0 |
|  | 5-FU treated | 0 | 0 |
|  | 5-FU + 28 | 2579 ± 318 | 3962 ± 2178 |

Groups of 3 cynomolgous monkeys are treated with 5-FU at 125 mg/kg and beginning 24 hours later treated with test compound s.c. at 0.05 mg/kg. The data reported are from sera taken 4 hours after test compound treatment.

TABLE 7

Effect of Test Compounds on Neutrophil Recovery in Cytoxan Treated Primates
Absolute Neutrophil Count/cu. mm. of Blood

| Ex. No. | Days after Cytoxan | Cytoxan | Cytoxan + Ex. 32 |
|---|---|---|---|
| 32 | 0 | 3640 ± 1058 | 3554 ± 1194 |
|  | 1 | 4900 ± 971 | 7849 ± 1592 |
|  | 2 | 2689 ± 156 | 4679 ± 867 |
|  | 3 | 1935 ± 126 | 1080 ± 264 |
|  | 4 | 1442 ± 344 | 370 ± 171 |
|  | 5 | 856 ± 295 | 455 ± 208 |
|  | 6 | 1009 ± 292 | 518 ± 218 |

TABLE 7-continued

Effect of Test Compounds on Neutrophil Recovery in Cytoxan Treated Primates

Absolute Neutrophil Count/cu. mm. of Blood

| Ex. No. | Days after Cytoxan | Cytoxan | Cytoxan + Ex. 32 |
|---|---|---|---|
| | 7 | 852 ± 301 | 1304 ± 1046 |
| | 8 | 542 ± 233 | 1596 ± 1000 |
| | 9 | 441 ± 194 | 2041 ± 423* |
| | 10 | 1244 ± 509 | 3506 ± 1130 |
| | 11 | 2053 ± 1002 | 4576 ± 673 |
| | 12 | 1885 ± 678 | 3761 ± 1394 |
| | 13 | 3502 ± 2297 | 3751 ± 1278 |
| | 14 | 3816 ± 1674 | 3106 ± 520 |

Groups of 4 cynomolgous monkeys are treated on day 1 and day 0 with cytoxan at 60 mg/kg. Beginning 24 hours after the second cytoxan dose, one group is treated daily s.c. with 50 μg/kg of test compound and the other with vehicle (water) only.
*p < 0.05 versus cytoxan only control by Student's t test.

TABLE 8

The Test Compounds Act Synergistically with c-kit ligand (KL) in Expanding Bone Marrow Progenitor cells in vitro

| Example No. | In vitro Culture | Fold Increase in CFU |
|---|---|---|
| 28 | medium alone | 0 |
| | test compound | 1.3 |
| | KL | 66 |
| | KL + test compound | 158 |

Bone marrow cells from 5-FU treated mice are used to enrich for early progenitor cells. The cells are split into 2 aliquots as described in the methods section for the "delta assay." The fold increase is determined by measuring the effect of a 7 day in vitro incubation of the cells with tissue culture medium plus test compound and/or growth factor KL on colony forming dells (CFU). The number of CFUs are then compared with colony formation of the fresh bone marrow cells that were not incubated in vitro to determine the fold increase. Test compound is used in vitro at 0.5 μg/ml.

TABLE 9

Effect of Oral Dosing with Test Compound on Neutrophil Recovery in 5-FU Treated Mice

| Example No. | Dose (mg/kg) | Neutrophils/cu. mm |
|---|---|---|
| 28 | 0 | 178 ± 64 |
| | 10 | 1391 ± 350 |
| | 1 | 765 ± 209 |
| | 0.1 | 81 ± 35 |
| *32 | 10 | 1844 ± 814 |
| | 1 | 547 ± 232 |
| | 0 | 67 ± 22 |

*Day 7 post 5-FU

Groups of 5 mice are treated with 150 mg/kg of 5-FU. One day later, daily oral dosing with test compounds begins and continues for 10 days. Data shown are from day 6 after 5-FU treatment.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing; for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 15 μg to about 100 μg/kg of animal body weight, preferably given in divided doses two to four times a day, or in sustained release form. For most large mammals the total daily dosage is from about 1 to 50 μg, preferably from about 1 to 20 μg. Dosage forms suitable for internal use comprise from about 5 μg to 25 μg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Abbreviations IL: interleukin CSF: colony stimulating factor G(granulocyte)-, M(macrophage)-, and GM(granulocyte-macrophage)- CSF's.

Ala: alanine

A₂pm: 2,6-diaminopimelic acid
Lys: lysine
Ser: serine
Thr: threonine
BOC: t-butoxycarbonyl
BOP benzotriazolyloxytris(dimethylamino) phosphonium hexafluorophosphate
CBZ: carbobenzyloxy
TFA: trifluoroacetic acid
MS: molecular sieves
TEA: triethylamine
DMAP: dimethylaminopyridine
TFA: trifluoroacetic acid
G(granulocyte)-, M(macrophage)-, and GM(granulocyte-macrophage)- CSF's The compounds of this invention and their preparation can be understood further by the following examples, but should not constitute a limitation thereof.

In the following examples, unless otherwise specified, products are separated by flash chromatography on Silica Gel 60—(230–400 mesh). The purity of products is determined by TLC on Silica Gel GF (250 mm). Melting points are obtained on a Mel-Temp apparatus and are uncorrected (all temperatures in °C.). Unless otherwise specified, 1H NMR (300 MHz) spectra are obtained for deuterochloroform solutions (1% internal standard, Me₄Si; coupling constants reported in Hz units). Reactions requiring anhydrous conditions are performed under argon atmosphere, using solvents in septum sealed bottles. Organic solutions are dried over magnesium sulfate or sodium sulfate and the solvents are removed in vacuo on a rotary evaporator.

EXAMPLE 1

N-(1-oxoheptyl)-D-allo-Threonine (2c-1)

A solution of n-heptanoyl chloride (440 mL, 2.83 mmol) in THF (250 mL) is added dropwise, over a period of 30 min, to a cold (−5 to 0° C., vigorously stirred mixture of D-allo-Thr (300 mg, 2.51 mmol) and 2N aq. NaOH (3.5 mL, 7.0 meq) in THF (4.0 mL). The resulting mixture is stirred for 2 h at the same temperature and overnight at room temperature. The volatiles are removed and the residue is diluted with o water and acidified, using conc. HCl. The mixture is extracted with EtOAc and the combined organic solution is washed with brine, dried, filtered, and concentrated to provide crude 2c-1 (420 mg, containing 10% excess heptanoyl reagent) which solidifies upon standing. NMR δ1.28 (d, J=6.5, 3H), 4.20 (m, 1H), 4.61 (dd, J=3.4, 6.6, 1H), 6.56 (br d, J=6.9, 1H); $[\alpha]_D^{26}$ −38±2 (CHCl₃).

EXAMPLE 2

N-(1-oxoheptyl)-D-Threonine (2c-2)

D-Thr (2.50 g, 20.99 mmol) is converted to 2c-2, following the procedure described in Example 1: NMR δ1.22 (d, J=6.4, 3H), 4.45 (m, 1H), 4.55 (dd, J=1.9, 8.3, 1H), 6.30–6.80 (br s, variable, >2H), 6.88 (br d, J=8.3, 1H); MS (HR-EI) m/z 321.1939 (M calcd. for C₁₈H₂₇NO₄, 321.1940).

EXAMPLE 3

N-(1-oxoheptyl)-L-allo-Threonine (2c-3)

L-allo-Thr (150 mg, 1.26 mmol) is converted to 2c-3, following the procedure described in Example 1: NMR same as that of 2c-1.

EXAMPLE 4

N-(1-oxoheptyl)-L-Threonine (2c-4)

L-Thr (300 mg, 2.51 mmol) is converted to 2c-4, following the procedure described in Example 1: NMR same as that of 2c-2.

EXAMPLE 5

N-(1-oxoheptyl)-D-Serine (2c-5)

D-Ser (6.00 g, 57.09 mmol) is converted to 2c-5, following the procedure described in Example 1. The crude product is purified by chromatography (2×21 cm column, gradient 1% CH₃OH and 0.5% HOAc to 3% CH₃OH and 2% HOAc in CH₂Cl₂): NMR (CD₃OD) δ0.90 (t, J=6.8, 3 H), 1.32 (m, 6H), 1.63 (m, 2H), 2.27 (apparent t, J≃7.5, 2H), 3.81 and 3.89 (AB of ABX, $J_{AB}$=11.2, $J_{AX}$=4.1, J BX=5.0, 2H), 4.49 (X of ABX, J 4.2, 4.8, 1 H); MS (CI, NH₄) m/z 218 (M+H), 235 (M+NH₄)]; $[\alpha]_D^{26}$ −8±1 (MeOH).

EXAMPLE 6

N-[trans(4-pentylcyclohexyl)carbonyl]-D-allo-Threonine (2c-6)

A solution of trans-4-pentylcyclohexane carboxylic acid (198 mg, 1.0 mmol) in dry toluene (1 mL) is treated with oxalyl chloride (760 mg, 5.9 mmol) at 0° C. and the mixture is stirred for 2 h at the same temperature and 1 h at room temperature. Excess reagent is removed in vacuo. A solution of the crude acid chloride in dry acetonitrile (2 mL) is added to a mixture of D-allo-Thr (100 mg, 0.85 mmol), 2N aq. NaOH (600 μl, 1.20 meq) and TEA (85 mg, 0.85 mmol) in THF (1.5 mL), following the procedure described in Example 1. The crude product 2c-6 is purified by chromatography (1.5×18 cm column, 5% CH₃₀H and 0.4% HOAc in CH₂Cl₂): NMR δ0.88 (t, J≃7, 3H), 4.15 (m, 1 H), 4.54 (m, 1H), 6.49 (d, 1H); MS (CI, CH₄) m/z 300 (M+H).

EXAMPLE 7

N-[(4-butoxyphenyl)acetyl]-D-allo-Threonine (2c-7)

4-Butoxyphenylacetic acid (288 mg, 1.38 mmol) is converted to the acid chloride and added to D-allo-Thr (150 mg, 1.26 mmol) to get 2c-9, following the procedure described in Example 6. The crude product is purified by chromatography (2.5×18 cm column, gradient 4% CH₃₀H and 0.3% HOAc in CH₂Cl₂): NMRδ0.96 (t, J=7.4, 3H), 1.14 (d, J=5.8, 3H), 1.47 (m, 2H), 1.74 (m, 2H), 3.53 (br s, 2H), 3.91 (t, J≃6.5, 2H), 4.10 (br s, 1H), 4.53 (br s, 1H), 4.90 (br s, >2H), 6.76 (br d, J=6.0, 1H), 6.84 (d, J=8.4, 2 H), 7.13 (d, J=8.4, 2H); MS (HR=EI) m/z 309.1567 (M calcd. for C₁₆H₂₃NO₅, 309.1576); $[\alpha]_D^{26}$−26±2 (CHCl₃); m.p. 90–94° C.

EXAMPLE 8

N-(1-oxoheptyl)-D-allo-Threonine Phenylmethyl Ester (2e-1)

Crude 2c-1 (420 mg, 1.82 mmol) is dissolved in DMF (18 mL) and treated with solid NaHCO₃ (321 mg, 3.82 mmol), and the resulting mixture is stirred for 1 h at 70°–75° C. The mixture is cooled to 40°–50° C. and treated with benzyl bromide (1.13 mL, 9.31 mmol). Stirring is continued for 2 h at 40° C. and 18 h at ambient temperature. The volatiles are removed, and the residue is taken up in H₂O/EtOAc. The organic layer is separated, washed with brine, dried, filtered, and evaporated. Purification of the crude product by chromatography (2×24 cm column, 3:1 hexane/EtOAc) gives a white solid which is characterized as 2e-1 (506 mg, 1.57 mmol): NMR δ0.88 (apparent t, J=6.8, 3H), 1.09 (d, J=6.4, 3H), 1.20–1.40 (m, 6H), 1.55–1.74 (m, 2H), 2.27 (apparent t, J≈7.5, 2H), 3.20–3.80 (br s, variable, 1H), 4.21 (dq, J=3.3, 6.4, 1H), 4.74 (dd, J=3.3, 6.8, 1H), 5.20 and 5.23 (AB, J=12.2, 2H), 6.43 (br d, J=6.5, 1H), 7.36 (m, 5H); MS (HR-EI) m/z 321.1939 (M calcd. for $C_{18}H_{27}NO_4$, 321.1940); $[\alpha]_D^{26} -29\pm2$ (CHCl$_3$); m.p. 70°–73° C.

EXAMPLE 9

N-(1-oxoheptyl)-D-Threonine Phenylmethyl Ester (2e-2)

Benzylation of crude 2c-2, according to the method of Example 10, provides 2e-2. The crude solid is purified by chromatography (3.0×39 cm column, 3:1 hexane/EtOAc): NMR δ0.88 (apparent t, J≈6.8, 3H), 1.20 (d, J=6.4, 3H), 1.23–1.38 (m, 6H), 1.60–1.71 (m, 2H), and 1.55–1.95 (overlapping br s, Variable, >1H), 2.28 (apparent t, J≈7.6, 2H), 4.37 (dq, J=2.4, 6.4, 1H), 4.67 (dd, J=2.4, 8.9, 1H), 5.19 and 5.22 (AB, J=12.3, 2H), 6.21 (br d, J≈9, 1H), 7.35 (m, 5H). MS (HR-EI) m/z 322.2011 (M+H calcd. for $C_{18}H_{28}NO_4$, 322.2019); $[\alpha]_D^{26} +9\pm1$ (CHCl$_3$); m.p. 77°–80° C.

EXAMPLE 10

N-(1-oxoheptyl)-L-allo-Threonine Phenylmethyl Ester (2e-3)

Benzylation of crude 2c-3, according to the method of Example 10, provides 2e-3. The crude solid is purified by chromatography (2.5×28 cm column, 4:1 hexane/EtOAc): NMR same as that of 2e-1; MS (HR-EI) m/z 321.1935 (M calcd. for $C_{18}H_{27}NO_4$, 321.1940); $[\alpha]_D^{26} +25\pm2$ (CHCl$_3$); m.p. 70°–73° C.

EXAMPLE 11

N-(1-oxoheptyl)-L-Threonine Phenylmethyl Ester (2e-4)

Benzylation of crude 2c-4, according to the method of Example 10, provides 2e-4. The solid is purified by chromatography (2.0×20 cm column, gradient of 4:1 to 3:1 hexane/EtOAc): NMR same as that of 2e-2: MS (HR-EI) m/z 321.1947 (M calcd. for $C_{18}H_{27}NO_4$, 321.1940); $[\alpha]_D^{26} -9\pm2$ (CHCl$_3$); m.p. 78°–80° C.

EXAMPLE 12

N-(1-oxoheptyl)-D-Serine Phenylmethyl Ester (2e-5)

Benzylation of 2c-5, according to the method of Example 10, provides 2e-5. NMR δ0.88 (apparent t, J≈6.8, 3 H), 1.20–1.40 (m, 6H), 1.55–1.70 (m, 2H), 2.25 (apparent t, J≈7.7, 2H), 2.45 and 2.80 (br s, 1H), 3.92 and 3.99 (AB of ABX, $J_{AB}$=11.2, $J_{AX}$=3.4, $J_{BX}$=4.0, 1H), 4.72 (ddd, apparent quintet, $J_{X-NH}$=7.3, $J_{AX}$≈$J_{BX}$ 3.7, 1H), 5.21 (apparent s, small AB side signals, 2H), 6.46 (br d, J=7.1, 1H), 7.36 (m, 5 H); MS (HR-EI) m/z 307.1792 (M calcd. for $C_{17}H_{25}NO_4$, 307.1801); $[\alpha]_D^{26} -11\pm1$ (CHCl$_3$); m.p. 62°–66° C.

EXAMPLE 13

N-[trans(4-pentylcyclohexyl)carbonyl]-D-allo-Threonine Phenylmethyl Ester (2e-6)

Benzylation of 2c-6, according to the method of Example 10, followed by chromatography (2×18 cm column, 0.5% CH$_3$OH in CH ), provides 2e-6. NMR δ0.88 (m, 5H), 1.07 (d, J=6.4, 3H), 1.10–1.35 (m, 8H), 1.35–1.55 (m, 2H), 1.64 (br s, 1H), 1.64–1.97 (m, 4H), 2.14 (m, 1H), 3.67 (br s, 1H), 4.20 (m, 1H), 4.73 (dd, J=3.2 and 6.7, 1H), 5.18 and 5.25 (AB, $J_{AB}$=12.2, 2 H), 6.44 (d, J=6.6, 1H); MS (HR-EI) m/z 389.2566 (M calcd. for $C_{23}H_{35}NO_4$, 389.2566); $[\alpha]_D^{26} -24\pm2$ (CHCl$_3$); m.p. 130°–34° C.

EXAMPLE 14

N-[(4-butoxyphenyl)acetyl]-D-allo-Threonine Phenylmethyl Ester (2e-7)

Benzylation of 2c-7, according to the method of Example 10, followed by chromatography (2×20 cm column, 3:1 hexane/EtOAc), provides 2e-7. NMR δ1.00 (m, 6H), 1.50 (m, 2H), 1.76 (m, 2H), 3.38 (br s, 1H), 3.56 (apparent s, small AB side signals, 2H), 3.95 (apparent t, J=6.5, 2H), 4.15 (m, 1H) 4.72 (dd, J=and 3.4, 1H), 5.13 and 5.19 (AB, J=12.2, 2H), 6.38 (br d, J=6.8, 1H), 6.87 (d, J=8.7, 2H), 7.15 (d, J=8.6, 2H); MS (CI, CH$_4$) m/z 400 (M+H); $[\alpha]_D^{26} -18\pm2$ (CHCl$_3$); m.p. 80°–83° C.

EXAMPLE 15

(R)-3-(Hydroxy-N-(1-oxoheptyl)-D-norvaline phenylmethyl ester (2e-8)

Benzylation of 2c-8, from Example 51, according to the method of Example 10, provides 2e-8.

EXAMPLE 16

(S)-3-(Hydroxy-N-(1-oxoheptyl)-D-norvaline phenylmethyl ester (2e-9)

Benzylation of 2c-9, from Example 52, according to the method of Example 10, provides 2e-9.

EXAMPLE 17

N-[N$^2$-[(1,1-dimethylethoxy)carbonyl]-N$^6$-[(phenylmethoxy)carbonyl]-(R)-6-[(phenylmethoxy)carbonyl]-L-lysyl]-D-Alanine Phenylmethyl Ester (40b)

A mixture of N-[N$^2$-[(1,1-dimethylethoxy)carbonyl]-N$^6$-[(phenylmethoxy)-carbonyl]-(R)-6-[(methoxy)carbonyl]-L-lysyl]-D-alanine 4-nitrophenylmethyl ester (40a, Kolodziejczyk, et. al., Int. J. Pept. Prot. Res., 1992, 39, 382; 683 mg, 1.06 mmol), 4 molecular sieves (2.15 g, crushed), THF (10.5 mL), and benzyl alcohol (11.0 mL, 105.6 mmol) is stirred for 30 min and then treated with titanium(IV) isopropoxide (82 μl, 0.27 meq). The resulting mixture is heated for 24 h at 85°–90° C. The solids are filtered through diatomaceous earth and the solvent removed. The excess benzyl alcohol is removed by distillation on a Kugelrohr apparatus (approx. 1000μ pressure, 50°–75° C.) The crude orange oil is chromatographed (2.5×31 cm column), gradient of 4:1–2:1 hexane/EtOAc) to provide 40b (633 mg, 88% yield): NMR δ1.39 (d, J=7.2, 3H), 1.43 (s, 9H), 1.40–1.67 (m, 4H), 1.84 (br s, 2H), 4.07 (br s, 1H), 4.40 (m, 1H), 4.58 (apparent quintet, 1H), 5.0 (br d, 1H), 5.07–5.25 (m, 6H), 5.43 (br d, J=7.9, 1 H), 6.68 (br d, 1H), 7.33 (m); MS (HR-FAB) m/z 676.3232 (M+H, calcd. for $C_{37}H_{46}N_3O_9$, 676.3234).

EXAMPLE 18

N-[N$^6$-[(phenylmethoxy)carbonyl]-(R)-6-[(phenylmethoxy)carbonyl]-L-lysyl]-D-Alanine Phenylmethyl Ester (3b)

A solution of 40b (251 mg, 0.37 mmol) in TFA (870 μl) is stirred for 30 min at 0° C. The TFA is removed and the oil is taken up in EtOAc and washed with saturated NaHCO$_3$ solution. Drying and removal of the solvent gives 3b (225 mg, slight excess) which is used in subsequent reactions without further handling: NMR δ1.39 (d, 3H) and 1.20–1.70 (overlapping m, 4H), 1.82 (br s, 2H), 3.23 (br s, variable, 2H), 3.33 (br s, 1H), 4.39 (m, 1H), 4.47 (apparent quintet, 1H), 5.03–5.13 (m, 6H), 5.27 (br d, 1H), 7.35 (m, 15H), 7.95 (br d, 1H); MS (FAB) m/z 576 (M+H), 598 (M+Na).

EXAMPLE b 19

R-(R*,R*)1-N-[N²-[[3-oxo-2-[(1-oxoheptyl)amino1-methyl-3-(phenylmethoxy)-propoxy]carbonyl]-N⁶-[(phenylmethoxy)carbonyl]-(R)-6-[(phenylmethoxy)-carbonyl]-L-lysyl]-D-Alanine Phenylmethyl Ester (1a-1)

A solution of 2e-1 (173.6 mg, 0.54 mmol) in THF (Sure/Seal solvent redried over 3_MS, 1.45 mL) is added to excess cold phosgene (1.92 M solution in toluene; 1.40 mL, 2.63 mmol), alternately with TEA (81 μl, 0.58 mmol) over a period of 15 min at 0° C. The resulting milky mixture is stirred for an addition 15 min at the same temperature and for 5 h at room temperature. The mixture is degassed with argon for 30 min and stirred under aspirator pressure for 30 min. The residue is treated With a solution of freshly prepared 3b (0.37 mmol) in CH₃CN (redried as for THF, 2.9 mL) and then TEA (81 μl, 0.58 mmol), both added all at once. The white slurry is stirred overnight at ambient temperature. The mixture is taken up in EtOAc/H₂O and the layers separated. The aq. phase is extracted with EtOAc twice and the combined organic phase is washed with brine, dried, filtered, and evaporated. Purification of the product by chromatography (3×30 cm column, gradient of 2:1–1:2 hexane/EtOAc) gaves a white wax which is identified as 1a-1: NMR δ0.86 (m, 3H), 1.11 (d, J=6.4, 3H), 1.20–1.40 (m, 8H), 1.42 (d, J=7.3, 3H), 1.50–1.75 (m, 4H, With overlapping H₂O signal), 1.75–2.05 (br d, 2H), 2.20 (m, 2H), 4.15 (br s, 1H), 4.47 (br s, 1H), 4.62 (apparent quintet, 1H), 4.87 (apparent br d, J≈6, 1H), 5.00–5.20 (m, 9H), 5.23 (m, 1H), 5.37 (br d, 1H), 6.40 (br d, 1H), 7.33 (m, 20H), 7.77 (br d, 1H); MS (HR-FAB) m/z 923.4420 (M+H, calcd. for C₅₁H₆₃N₄O₁₂, 923.4442).

EXAMPLE 20

[S-(R*,S*)1-N-[N²-[[3-oxo-2-[(1-oxoheptyl)amino1-methyl-3-(phenylmethoxy)-propoxy]carbonyl]-N⁶-[(phenylmethoxy)carbonyl]-(R)-6-[(phenylmethoxy)-carbonyl]-L-lysyl]-D-Alanine Phenylmethyl Ester (1a-2)

Compound 2e-2 (20 mg, 0.062 mmol) is coupled with 3b (0.043 mmol), following the procedure in Example 19. Purification of the crude product (1.5×21 cm column, 2:1 hexane/EtOAc) gives a white wax which is characterized as 1a-2: NMR δ0.87 (m, 3H), 1.25 and 1.23–1 38 (overlapping d, J=6.2, 3H and m, 8H), 1.40 (d, J=7.2, 3H), 1.55–1.75 (m, 4H, with overlapping H₂O signal), 1.75–1.90 (m, 2H), 2.29 (m, 2H), 4.08 (br s, 1H), 4.83 (br s, 1H), 4.58 (apparent quintet, 1H), 4.83 (br d, 1H), 5.05–5.30 (m, 9H), 5.35 (br s, 1H), 5.68 (br s, 1H), 6.30 (br s, 1H), 6.62 (br s, 1H), 7.33 (m, 20H); MS (HR-FAB) m/z 923.4455 (M+H, calcd. for C₅₁H₆₃N₄O₁₂, 923.4442).

EXAMPLE 21

[S-(R*,R*)]-N-[N²-[[3-oxo-2-[(1-oxoheptyl)amino]-methyl-3-(phenylmethoxy)-propoxy]carbonyl]-N⁶-[(phenylmethoxy)carbony]-(R)-6-[(phenylmethoxy)carbonyl]-L-lysyl]-D-Alanine Phenylmethyl Ester (1a-3)

Compound 2e-3 (27.4 mg, 0.085 mmol) is coupled with 3b (0.06 mmol), following the procedure in Example 19. Purification of the crude product (1.5×16 cm column, 2:1 hexane/EtOAc) gives a white wax which is identified as 1a-3: NMR δ0.86 (m, 3H), 1.20–1.35 (m, 1H), 1.39 and 1.35–1.57 (overlapping d, J=7.1, 3H, and m, 4H), 1.75–1.95 (br s, 2H), 2.10–2.30 (m, 2H), 4.08 (br m, 1H), 4.37 (br s, 1H), 4.57 (apparent quintet, J=7.3, 1H), 4.70–5.30 (overlapping multiplets, 10H), 5.93 (br d, 1H), 6.50 (br d, 1H), 6.63 (br d, J=7, 1H), 7.05 (m, 1H), 7.34 (m, 20H); MS (HR-FAB) m/z 945.4281 (M+Na, calcd. for C₅₁H₆₂N₄O₁₂Na, 945.4262).

EXAMPLE 22

[R-(R*,S*)]-N-[N²-[[3-oxo-2-[(1-oxoheptyl)amino1-methyl-3-(phenylmethoxy)-propoxy]carbonyl]-N⁶-[(phenylmethoxy)carbony]-(R)-6-[(phenylmethoxy)carbonyl]-L-lysyl]-D-Alanine Phenylmethyl Ester (1a-4)

Compound 2e-4 (27.6 mg, 0.085 mmol) is coupled with 3b (0.06 mmol), according to the procedure in Example 19. Purification of the crude product (1.5 ×16 cm column, gradient 2:1–1:1 hexane/EtOAc) gives a white wax Which is identified as 1a-4: NMR δ0.86 (m, 3H), 1.25 and 1.25–1.40 (overlapping d, J =6.5, 3 and m, 11H), 1.42 (d, J =7.0, 3H), 1.53–1.73 (m, 4H, with overlapping H20 signal), 1.73–1.95 (br s, 2H), 2.27 (apparent t, J≈7.5, 2H), 4.12 (br s, 1H), 4.38 (br s, fine structure, 1H), 4.58 (br s, 1H), 4.81 (br d, 1H), 5.03–5.23 (m, 8H), 5.23–5.48 (m, 3H), 6.41 (br d, 1H), 6.71 (br d, 1H), 7.33 (m, 20H); MS (HR-FAB) m/z 945.4271 (M+Na, calcd. for C₅₁H₆₂N₄O₁₂Na, 945.4262).

EXAMPLE 23

(R)-N-[N²-[[3-oxo-2-[(1-oxoheptyl)amino]-3-(phenylmethoxy)propoxy]carbonyl]-N⁶-[(phenylmethoxy)carbonyl]-(R)-6-[(phenylmethoxy)carbonyl]-L-lysyl]-D-Alanine Phenylmethyl Ester (1a-5)

Compound 2e-5 (99 mg, 0.32 mmol) is coupled with 3b (0.21 mmol), following the procedure in Example 19. Purification of the crude product (2×21 cm column, gradient 2:1–1:1 toluene/ether) gives a white wax which is characterized as 1a-5: NMR δ0.88 (m, 3 H), 1.20–1.38 (m, 8H), 1.39 (d, J =7.2, 3H), 1.50–1.66 (m, 4H), 1.85 (br s, 2H), 2.21 (apparent t, J≈7.6, 2H), 4.09 (br s, 1H), 4.23–4.51 (m, 3H), 4.58 (apparent quintet, J=7.3, 1H), 4.90 (br s, 1 H), 5.05–5.25 (m, 9H), 5.55 (br t, 1H), 6.55 (br d, 1 H), 6.90 (br d, 1H), 7.33 (m, 20H); MS (HR-FAB) m/z 909.4270 (M+H, calcd. for C₅₀H₆₁N₄O₁₂, 909.4285).

EXAMPLE 24

[R-(R*,R*)]-N-[N²-[[1-methyl-3-oxo-2-[(4-pentyl cyclohexyl)carbonyl]amino1-3-(phenylmethoxy) propoxy]carbonyl]-N⁶-[(phenylmethoxy)carbonyl]-(R)-6-[(phenylmethoxy)carbonyl]-L-lysyl]-D-Alanine Phenylmethyl Ester (1a-6)

Compound 2e-6 (33 mg, 0.085 mmol) is coupled with 3b (0.06 mmol), following the procedure in Example 19. Purification of the crude product (1.5×17 cm column, 2:1 hexane/EtOAc) gives a white wax which is characterized as 1a-6: NMR δ0.87 (m, 5H), 1.10 (d, J=6.6, 3 H), 1.10–1.43 (m, 15H), 1.43 (d, J=7.3, 3H), 1.70–2.20 (m, 7H), 4.15 (m, 1H), 4.37 (m, 1H), 4.64 (m, 1H), 4.89 (br d, J=8.3, 1H), 5.03–5.30 (m, 9 H), 5.37 (br d, 1H), 6.43 (br d, 1H), 7.33 (m, 20H), 7.34 (br d, 1H); MS (HR-FAB) m/z 1013.4903 (M+Na, calcd. for $C_{56}H_{70}N_4O_{12}Na$, 1013.4888).

EXAMPLE 25

[R-(R*,R*)]-N-[N²-[2-[[(4-butylphenyl)acetyl]amino]-1-methyl-3-oxo-3-(phenylmethoxy)propoxy]carbonyl]-N⁶-(phenylmethoxy)carbonyl]-(R)-6-[(phenylmethoxy)carbonyl]-L-lysyl]-D-Alanine Phenylmethyl Ester (1a-7)

Compound 2e-7 (34 mg, 0.085 mmol) is coupled with 3b (0.06mmol), following the procedure in Example 19. Purification of the crude product (1.5×14 cm column, 2:1 hexane/EtOAc) gives a white wax which is characterized as 1a-7: NMR & 0.97 (m, 6H), 1.10–1.60 (m, overlapping d, J=7.3, 9H), 1.65–2.03 (m, 4H), 3.45 (m, 2H), 3.92 (apparent t, J=6.5, 2H), 4.15 (m, 1H), 4.38 (m, 1H), 4.62 (apparent quintet, J=7.3, 1H), 4.86 (br d, J=8.0, 1H), 5.05–5.25 (m, 9 H), 5.42 (br d, J=7.5, 1H), 6.33 (br d, 1H), 6.84 (d, J=8.5, 2H), 7.13 (d, J=8.5, 2H), 7.33 (m, 20 H), 7.89 (br d, 1H); MS (HR-FAB) m/z 1023.4368 (M+Na, calcd. for $C_{56}H_{64}N_4O_{12}Na$, 1023.4368).

EXAMPLE 26

[R-(R*,R*)]-N-[N²-[[1-Ethyl-3-oxo-2-[(1-oxoheptyl)amino]-3-(phenylmethoxy)propoxy]carbonyl]-N⁶-[(phenylmethoxy)carbonyl]-(R)-6-[(phenylmethoxy)-carbonyl]-L-tysyl]-D-Alanine Phenylmethyl Ester (1a-8)

Compound 2e-8 (99 mg, 0.32 mmol) is coupled with 3b (0.21 mmol), following the procedure in Example 19.

EXAMPLE 27

[S-(R*,S*)]-N-[N²-[[1-Ethyl-3-oxo-2-[(1-oxoheptyl)amino]-3-(phenylmethoxy)propoxy]carbonyl1-N⁶-[(phenylmethoxy)carbonyl]-(R)-6-[(phenylmethoxy)-carbonyl]-L-tysyl]-D-Alanine Phenylmethyl Ester (1a-9)

Compound 2e-9 (99 mg, 0.32 mmol) is coupled with 3b (0.21 mmol), following the procedure in Example 19.

EXAMPLE 28

[R-(R*,R*)]-N-(R)-6-carboxy-N²-[[2-carboxy-1-methyl-2-[(1-oxoheptyl)amino]ethoxy]carbonyl]-L-lysyl]-D-Alanine (1a-11)

A solution of 1a-1 (140 mg, 0.15 mmol) in EtOAc-/EtOH (5 mL:15 mL) is hydrogenated over Pd(OH)₂ (Pearlman's catalyst, 20% on C, 100 mg) using a Parr apparatus at an initial pressure of 70 psi. After 5.5 h, filtration and evaporation gives a colorless glass. The latter is triturated with ether and the sides of the flask are scraped to provide a white crystalline powder. The ether solution is removed with a syringe and the solid is washed with two more portions of ether, dried, and characterized as 1a-11: NMR (CD₃OD) δ0.89 (m, 3H), 1.22 (d, J=6.5, 3H), 1.24–1.39 (m, 6H), 1.42 (d, J=7.3, 3H), 1.45–1.99 (m, 8H), 2.26 (t, J=7.5, 2H), 3.62 (m, 1H), 4.06 (m, 1H), 4.41 (m, 1H), 4.89 (br s for OH, NH; one hidden CH signal), 5.14 (m, 1H); MS (HR-FAB) m/z 519.2671 (M+H calcd. for $C_{22}H_{39}N_4O_{10}$, 519.2666).

EXAMPLE 29

[S-(R*,S*)]-N-[(R)-6-carboxy-N²-[[2-carboxy-1-methyl-2-[(1-oxoheptyl)amino]ethoxy]carbonyl]-L-lysyl]-D-Alanine (1a-12)

Hydrogenolysis of compound 1a-2 (37.0 mg, 0.04 mmol), according to the method of Example 28, yields 1a-12: NMR (CD₃OD) δ0.90 (m, 3H), 1.26 (d, J=6.3, 3H), 1.2–1.3B (m, 6H), 1.40 (d, J=7.2, 3H), 1.44–1.73 (m, 5H), 1.73–2.05 (m, 3H), 2.33 (apparent t, J≈7.3, 2H), 3.92 (m, 1H), 4.16 (br s, 1H), 4.38 (m, 1 H), 4.64 (m, 1H), 5.31 (m, 1H); MS (HR-FAB) m/z 519.2671 (M+H calcd. for $C_{22}H_{39}N_4O_{10}$, 010, 519.2666).

EXAMPLE 30

[S-(R*,R*)]-N-(R)-6-carboxy-N²-[[2-Carboxy-1-methyl-2-[(1-oxoheptyl)amino]ethoxy]carbonyl]-L-lysyl]-D-Alanine (1a-13)

Hydrogenolysis of compound 1a-3 (22.0 mg, 0.024 mmol), according to the method of Example 28, yields 1a-13: NMR (CD₃OD) δ0.91 (m, 3H), 1.19–1.45 [overlapping d (J=6.5, at 1.25 d), m, and d (J=7.3, at 1.39 d), 12 H], 1.47–1.72 (m, 5H), 1.72–2.10 (m, 3H), 2.29 (apparent t, J=7.5, 2H), 3.68 (m, 1H), 4.20 (m, 1 H), 5.17 (m, 1H); MS (HR-FAB) m/z 519.2651 (M+H calcd. for $C_{22}H_{39}N_4O_{10}$, 519.2666).

EXAMPLE 31

R-(R*,S*)]-N-(R)-6-carboxy-N²-[[2-carboxy-1-methyl-2-[(1-oxoheptyl)amino]ethoxy]carbonyl]-L-lysyl]-D-Alanine (1a-14)

Hydrogenolysis of compound 1a-4 (36.6 mg, 0.04 mmol), according to the method of Example 28, yields 1a-14: NMR (CD₃OD) δ0.90 (m, 3H), 1.22–1.36 [overlapping d (J=6.2, at 1.24 d) and m, 12H], 1.36–2.02 (m, 8H), 2.32 (m, 2H), 3.60–3.80 (m, 1H), 4.09 (m, 1H), 4.36 (m, 1H), 4.61 (m, 1H), 5.30 (br s, 1H); MS (HR-FAB) m/z 519.2667 (M+H calcd. for $C_{22}H_{39}N_4O_{10}$, 519.2666).

EXAMPLE 32

(R)-N-[(R)-6-carboxy-N²-[[2-carboxy-2-[(1-oxoheptyl)amino]ethoxy]carbonyl]-L-lysyl]-D-Alanine (1a-15)

Hydrogenolysis of compound 1a-5 (247 mg, 0.27 mmol), according to the method of Example 28, yields 1a-15: NMR (CD₃OD) δ0.90 (m, 3H), 1.16–1.46 [overlapping d (J=7.0, at 1.40 d) and m, 9H], 1.46–2.05 (m, 8H), 2.25 (m, 2H), 3.69 (br s, 1H), 4.11 (br s, 1H), 4.36 (m, 3H), 4.63 (br s, 1H); MS (HR-FAB) m/z 505.2505 (M +H calcd. for 505.2509).

EXAMPLE 33

[(R)-6-Carboxy-N²-[[2-carboxy-1-methyl-2-[[(4-pentylcyclohexyl)carbonyl]amino]ethoxy]carbonyl]-L-lysyl]-D-Alanine (1a-16)

Hydrogenolysis of compound 1a-6 (17 mg, 0.017 mmol), according to the method of Example 28, yields 1a-16: NMR (CD₃OD) δ0.90 (m, 5H), 1.10–1.75 [m, 19H, with overlapping 1.23 (d, J=6.6) and 1.45 (d, J=7.4)], 1.75–2.05 (m, 8H), 2.24 (m, 1H), 3.60 (m, 1H), 4.07 (m, 1H), 4.44 (m, 1H), 4.90 (m, 1H, under OH signal) 5.14 (m, 1H); MS (HR-FAB) m/z 609.3099 (M+Na, calcd. for $C_{27}H_{46}N_4O_{10}Na$, 609.3112).

EXAMPLE 34

N-[N²-[[2-[[(4-Butoxyphenyl)acetyl]amino]-2-carboxy-1-methylethoxy]carbonyl]-(R)-6-carboxy-L-lysyl]-D-Alanine (1a-17)

Hydrogenolysis of compound 1a-7 (33 mg, 0.034 mmol), according to the method of Example 28, yields 1a-17: NMR (CD₃OD) δ 0.99 (m, 3H), 1.10–2.05 (m, 16H), 3.55 (m, 2H), 3.65 (m, 1H), 3.96 (m, 2H), 4.07 (m, 1H), 4.38 (m, 1H), 4.90 (m, 1H, under OH signal), 5.18 (m, 1H), 6.85 (m, J=8.6, 2H), 7.22 (m, J=8.6, 2H); MS (HR-FAB) m/z 597.2757 (M+H, calcd. for $C_{27}H_{41}N_4O_{11}$, 597.2772).

EXAMPLE 35

[R-(R*,R*)]-N-[(R)-6-carboxy-N²-[1[-carboxy[(1-oxoheptyl)amino]methyl]propoxy]carbonyl]-L-lysyl]-D-Alanine (1a-18)

Hydrogenolysis of compound 1a-8 (247 mg, 0.27 mmol), according to the method of Example 28, yields 1a-18:

EXAMPLE 36

[S-(R*,S*)]-N-(R)-6-carboxy-N²-[[1-carboxy[(1oxoheptyl)amino]methyl]propoxy]carbonyl]-L-lysyl]-D-Alanine (1a-19)

Hydrogenolysis of compound 1a-9 (247 mg, 0.27 mmol), according to the method of Example 28, yields 1a-19

EXAMPLE 37

N-(1-Oxoheptyl)-L-Serine Methyl Ester (2j)

L-serine methyl ester hydrochloride is converted to 2j, according to the procedure described in Example 1: NMR δ 0.89 (t, J=6.9, 3H), 1.30 (m, 6H), 1.65 (m, 2H), 2.28 (apparent t, J≈7.5, 2H), 3.80 (s, 3H), 3.96 (m, 2H), 4.69 (m, 1H), 6.80 (br s, 1H); MS (HR-EI) m/z 231.1465 (M calcd. for $C_{11}H_{21}NO_4$, 231.1459); $[\alpha]_D^{26}$ +22±1 (CHCl₃).

EXAMPLE 38

(S)-2,2-Dimethyl-3-(1-oxoheptyl)-4-oxazolidinecarboxylic Acid Methyl Ester (8a)

Compound 2j (320 mg, 1.38 mmol) and p-TSA (40 mg) are dissolved in dry acetone (2 ml) and 2,2-dimethoxypropane (2 ml). The resulting solution is heated overnight at reflux. Solid K₂CO₃ is added and the volatiles removed in vacuo to give a residue. Flash chromatography (2×21 cm column, 6:1 hexane/EtOAc) of the residue provides 8a as an oil: NMR δ 0.88 (m, 3H), 1.29 (m, 6H), 1.57 (s, 3H), 1.62 (m, 2H), 1.70 (s, 3H), 2.15 (m, 2H), 3.81 (s, 3H), 4.20 (m, 2H), 4.46 (m, 1H); $[\alpha]_D^{26}$ = −47±1 (CHCl₃).

EXAMPLE 39

(R)-2,2-Dimethyl-3-(1-oxoheptyl)-4-oxazolidinemethanol

A solution of 8a (296 mg, 1.09 mmol) in dry ether (1 mL) is treated with lithium borohydride (2 M solution in THF, 0.55 mL, 1.09 meq) under an argon atmosphere. The mixture is stirred for 3 h at reflux and 18 h at room temperature. The resulting mixture is diluted with ether and quenched with methanol. The volatiles are removed and the residue is taken up in EtOAc/H₂O. Workup provides the crude alcohol which is purified by chromatography (2:1 hexane/EtOAc): NMR δ 0.88 (m, 3H), 1.30 (m, 6H), 1.54 (s, 3H), 1.62 (s, 3H), 2.35 (m, 2H), 3.30–4.40 (complex m, 6H); MS (HR-EI) m/z 243.1837 (M calcd. for $C_{13}H_{25}NO_3$ 243.1840); $[\alpha]_D^{26}$ = −5±1 (CHCl₃).

EXAMPLE 40

(S)-2,2-Dimethyl-3-(1-oxoheptyl)-4-oxazolidinecarboxaldehyde (9a)

A solution of oxalyl chloride (105 μl, 1.23 mmol) in CH₂Cl₂ (2.75 mL) is cooled to −60° C. A solution of DMSO (192 μL) in CH (0.55 mL) is added over a period of 5 min. and the resulting milky mixture is stirred for 15 min at −60° C. The alcohol from Example 39 (133 mg., 0.55 mmol) in CH₂Cl₂ (0.55 ml) is added to the mixture over 5 min. The bath is allowed to warm up to −20° C. (20 min.) and the clear solution is stirred for 20 min. at −20° C. Triethylamine (0.77 mL) and H₂O (3.4 mL) are added and the mixture is stirred for 5 minutes at ambient temperature. Workup with CH₂Cl₂ gives a crude oil which is purified by chromatography (1.5×20 cm, 3:1 together) to give 9a: NMR δ0.85 (m, 3H), 1.30 (m, 6H), 1.60 (s, 3H), 1.60–1.70 (m, 2H), 1.70 (s, 3H), 2.00–2.40 (m, 2H), 4.00–4.30 (m, 3H), 9.65 (d, J≈1,1H).

EXAMPLE 41

(4S)-α-Ethyl-2,2-dimethyl-3-(1-oxoheptyl)-4-oxazolidinemethanol (10a)

A solution of 9a (108 mg, 0.44 mmol) in ether (1 mL) is added dropwise to a cold (5°) solution of EtMgBr (3 M in ether, 0.36 mL). The cold bath is removed, a crystal of iodine is added to the mixture and stirring is continued for 1.5 h at room temperature. The resulting mixture is diluted with EtOAc and washed with saturated aqueous NH₄Cl solution. The aqueous phase is reextracted and the combined organic solution dried and evaporated to yield crude 10a: NMR δ0.88 (m, 3H), 1.05 (m, 3H), 1.30 (m, 6H), 1.45 (m, 2H), 1.57 (s, 3H), 1.50–1.75 (m, 5H), 2.10–2.60 (m, 2H), 3.50–4.50 (m, 4H); MS (EI) m/z 271 (M).

EXAMPLE 42

R-(R*,S*) and S-(R*,R*)-N-[2-hydroxy-1-(hydroxymethyl)butyl Heptanamide

Crude 10a (107 mg, 0.39 mmol) is dissolved in cold TFA (0.38 mL) containing H₂O (≈1%) and the solution is stirred for 45 min. at 0°. The volatiles are removed and the residue is taken up in EtOAc and washed with saturated NaHCO₃ and brine. After drying and removal of solvent, 11a (2:1 mixture of diastereomers) is isolated by chromatography (1.5×18 cm, 2% MeOH in CH₂Cl₂): NMR 0.85–1.05 (m, 6H), 1.30 (m, 6H), 2.23 (m, 2H), 3.65–4.05 (m, 4H), 6.20 and 6.40 (two broad d, 2:1 ratio, respectively, 1H); MS (HR-EI) m/z 231.1887 (M calcd. for $C_{12}H_{25}NO_3$, 231.1940).

EXAMPLE 43

[S-(R*,R*)]-N-[1-[[[(1,1-Dimethylethyl)diphenylsilyl]oxy]methyl]-2-hydroxybutyl]Heptanamide (10c)

A mixture of 11a (1.0 mmol), t-butyldiphenylsilyl chloride (1.2 mmol), TEA (1.2 mmol) and DMAP (0.04 mmol) in CH₂Cl₂ (1.5 mL) is stirred for 20 h at room temperature according to S. K. Chaudhary and O. Hernandez (*Tetrahedron Lett.*, 1979, 99). The resulting mixture is partitioned between CH₂Cl₂ and H₂O. The layers are separated and the organic phase washed with saturated NH4Cl solution and dried. Removal of solvent gives a mixture which is purified by chromatography. The less polar product is identified as 10c.

EXAMPLE 44

[R-(R*,S*)]-N-[1-[[[(1.1-Dimethylethyl)diphenylsilyl]oxy]methyl]-2-hydroxybutyl]Heptanamide (10d)

The more polar isomer isolated in Example 43 is characterized as 10d.

EXAMPLE 45

[S-(R*,R*)]-N-1-[[[(1,1-Dimethylethyl)diphenylsilyl]oxy]methyl]-2-(phenylmethoxy)butyl Heptanamide (12c)

A solution of 10c (1 mmol) in DMF (0.60 mL) and BnBr (0.96 mL, 8 mmol) is treated with n-Bu4N+I− (37 mg, 0.1 mmol). A dispersion of NaH (60% in oil, 1.3 meq) is added in portions to the solution over a period of 1 h. The mixture is stirred overnight at room temperature. Ether work-up provides a crude oil which is purified by chromatography. The major product is characterized as 12c.

EXAMPLE 46

[R-(R*,S*)]-N-[1-[[[(1,1-Dimethylethyl)diphenylsilyl]oxy]methyl]-2-(phenylmethoxy)butyl Heptanamide (12d)

Compound 12d is prepared from 10d, using the procedure of Example 45.

EXAMPLE 47

[S-(R*,R*)]-N-[1-(Hydroxymethyl)-2-(phenylmethoxy)butyl]Heptanamide (13c)

Compound 12c (1 mmol) is dissolved in THF (1.1 mL) and treated with n-Bu4N+F− solution (1N in THF, 3.0 mL; (according to E. J. Corey and A. Venkateswarlu, J. Amer. Chem. Soc., 1972, 94, 6190). After 40 min. at room temperature, the reaction is quenched with ice and the mixture partitioned between ether and water. The aqueous layer is reextracted with ether and the combined organic layers washed with brine, dried and the solvent removed to give 13c which is purified by chromatography.

EXAMPLE 48

[R-(R*,S*))-N-[1-(Hydroxymethyl)-2-(phenylmethoxy)butyl]Heptanamide (13d)

Compound 13d is prepared from 12d according to the procedure described in Example 47.

EXAMPLE 49

N-(1-Oxoheptyl)-3-(phenylmethoxy)-threo-D-Norvaline (14c)

Alcohol 13c (1 mmol) in DMF (4 mL) is treated with pyridinium dichromate (3.5 meq), according to the method of (Corey and Schmidt, Tetrahedron Lett., 1979, 399). After 18 h, the mixture is poured over ice. Ether workup gives 14c which is purified by chromatography.

EXAMPLE 50

N-(1-Oxoheptyl)-3-(phenylmethoxy)-erythro-D-Norvaline (14d)

Compound 14d is prepared from 13d following the procedure in Example 49.

EXAMPLE 51

3-Hydroxy-N-(1-oxoheptyl)-threo-D-Norvaline (2c-8)

A solution of 14c in EtOAc/EtOH is hydrogenated according to the procedure in Example 28. The crude product is identified as 2c-8 and used in Example 15.

EXAMPLE 52

3-Hydroxy-N-(1-oxoheptyl)-erythro-D-Norvaline (2c-9)

Compound 2c-9 is prepared from 14d following the procedure in Example 51. The crude product is used in Example 16.

EXAMPLE 53

$N^2$-(1-oxyheptyl)-D-Asparagine(22a)

D-Asparagine 21a (4.5 g, 29.9 mmol) is converted to 22a following the procedure of Example 1. A mixture of water and THF is used as solvent and the 2N aqueous NaOH is replaced with a mixture of triethylamine and 0.5N NaHCO3. The crude solid is purified by recrystallization from methyl alcohol-ether. NMR(CD3OD) δ0.90(t, 3H), 1.61(m, 2H), 2.23(t, 2H), 2.75(m, 2H), 4.71(dd, 1H);MS(LR-CI) m/z 245 (M+H) calcd for $C_{11}H_{21}N_2O_4$ 245.

EXAMPLE 54

3-Amino-N-(1-oxoheptyl)-D-Alanine(21-1)

Compound 22a (2.21 g, 9.0 mmol) is added to a solution of bis-(trifluoroacetoxy)iodobenzene (5.83 g, 13.57 mmol) in 51 mL of N,N-dimethylformamide and 41 mL of water. The mixture is stirred for 15 min. and treated with pyridine (1.46 mL, 18.09 mmol). The resulting solution is stirred for 18 h at room temperature. The volatiles are removed and the residue is diluted with 90 mL of water. The mixture is washed with 3×50 mL of ether. The aqueous layer is separated and evaporated. Trituration of the resulting liquid with ether gives a white solid which is characterized as 2q-1: NMR(CD3OH) δ0.61(t, 3H), 1.35(m, 2H), 2.05(t, 2H), 3.0–3.2(m, 2H), 4.40(m, 1H): MS(HR-FAB)m/z 217.1555 (M+H, calcd for $C_{10}H_{21}N_2O_3$, 217.1552)

EXAMPLE 55

3-Amino-N-(1-oxoheptyl)-D-Alanine Phenyl Methyl Ester Monohydrochloride (2h-1)

Acetyl chloride (3.05 mL, 42.87 mL is added dropwise over a period of 10 min. to an ice cold solution of benzyl alcohol (10 mL, 96.63 mmol). The resulting solution is stirred for an additional 30 min. The ice bath is then removed and compound 2g-1 (1.32 g, 6.12 mmol) is added. The solution is stirred overnight at room temperature and the volatiles removed by Kugelrohr distillation. The residue is triturated with ether and then recrystallized from ethyl alcohol to give a white solid which is identified as 2h-1: NMR (CDCl3) δ0.75(t, 3H), 1.45(m, 2H), 2.20(t, 2H), 3.40(m, 2H), 4.80(br s, 1H), 5.10(s, 2H), 7.62(br s, 1H); MS(HR-FAB) m/z 307.2017(M+H, calcd for $C_{17}H_{27}N_2O_3$ 307.2022).

EXAMPLE 56

[S-(R*,R*)]-N-[2-Hydroxy-1-(hydroxymethyl)propyl]-heptanamide (11c)

To a solution of (2e-2) (1.0 g, 3.11 mmol) in ether, with warming, is added dropwise at room temperature a solution of lithium borohydride (1.60 ml, 3.2 mmol) in tetrahydrofuran. The reaction mixture is refluxed tor 3 hours, diluted with ether and slowly treated with methanol until the fizzing stops. The volatiles are removed to give a residue which is partitioned between water and ethyl acetate. The organic layer is separated, washed with brine, dried and filtered. The filtrate is evaporated to a residual oil which is purified by chromatography by elution with 3:1 ethyl acetate-hexanes to give 560 mg of the desired product as an oil. NMR $\delta$1.20 (d, 3H), 1.65 (m, 2H), 2.26 (t, 2H), 4.19 (q, 1H), 6.23 (br d, 1H), MS (CI) m/z 218 (M+H calc'd for $C_{11}H_{24}NO_3$ 218).

EXAMPLE 57

[S-(R*,R*))-N-1-[[(1,1-Dimethylethyl)dimethylsily]oxy]methyyl]-2-hydroxypropyl]heptanamide (10c)

A mixture of 11c, (1.945 g) of t-butyldimethylsilyl chloride, (1.4165 g) of triethylamine (951 mg, 1.31 mL), and 4-dimethylaminopyridine (42.76 mg) in 13 mL of methylene chloride is stirred under argon at room temperature for 18 h. The reaction mixture is diluted with methylene chloride and water added. The organic layer is separated, washed with water, dried and evaporated to give 3.25 g of a residual oil which is purified by chromatography by elution with 1:5 ethyl acetate/hexane to give 2.30 g of the desired product as an oil. NMR $\delta$0.08 (d, 6H), 0.89 (t, 3H), 0.90 (s, 9H), 1.16 (d, 3H), 1.65 (m, 2H), 2.24 (t, 2H), 3.47 (s, 1H), 3.84 (m, 1H), 3.85 (s, 2H), 4.28 (q, 1H), 6.13 (brd, 1H); MS (FAB) m/z=332 (M+H calc'd for $C17H_{38}NO_3Si$ 332).

EXAMPLE 58

(S)-N-[1-[[[(1,1-dimethylethyl)dimethylsilyl]oxy]methyl]-2-oxopropyl]-Heptanamide (27c)

A mixture of (10c), (2.30 g, 6.94 mmol) and pyridinium dichromate (10.62 g, 28.2 mmol) in 20 mL of N,N-dimethylformamide is stirred under argon for 18 h. The reaction mixture is diluted with 100 mL of water and extracted with ethyl acetate (3×40 mL). The organic layer is separated, washed with water and brine, dried and evaporated to give 1.87 g of a residual brown liquid. The liquid is purified by chromatography using 1:6 ethyl acetate/hexane to give 997 mg of the desired product as an oil. NMR $\delta$0.83 (s, 9H), 1.61 (m, 2H), 2.22 (t, 2H), 2.23 (s, 3H), 3.82 (dd, 1H), 4.09 (dd, 1H), 4.57 (m, 1H), 6.42 (brd, 1H); MS (FAB) m/z 330 (M+H calc'd for $C_{17}H_{36}NO_3Si$ 330).

EXAMPLE 59

[R-(R*,S*)]-N-[1-[(1,1-dimethylethyl)dimethylsilyl]oxy]methyl]-2-[(phenylmethyl)amino]propyl]Heptanamide (28c)

A mixture of 27c (960 mg, 2.91 mmol) in 5 mL of methyl alcohol containing molecular sieves is stirred at room temperature for 30 min. While stirring, sodium cyanoborohydride (365 mg) is added and the reaction mixture stirred under argon for 18 h. The reaction mixture is filtered and evaporated to a residue which is partitioned between ethyl acetate and aqueous sodium bicarbonate. The organic layer is separated, washed with brine, and dried and evaporated to give 1.224 g of a residual yellow liquid. The residue is purified by chromatography using 2:5 ethyl acetate/hexane to give 561.2 mg of desired product 28c as an oil. NMR $\delta$0.84 (s, 9H), 1.09 (d, 3H), 1.61 (m, 2H), 2.20 (t, 2H), 3.08 (m, 1H), 6.22 (brd, 1H), 7.32 (m, 5H): MS (HR-FAB) m/z 421.3245 (M+H calc'd for $C_{24}H_{44}N_2O_2Si$ 421.3250).

EXAMPLE 60

[R-(R*,R*)]-N-[1-[[(1,1-dimethylethyl)dimethylsilyl]oxy]methyl]-2-[(phenylmethyl)amino]propyl]Heptanamide (28d)

Further elution of the chromatography column in Example 59 gives 239.4 of desired product 28d as an oil NMR $\delta$0.84 (s, 9H), 1.18 (d, 3H), 1.61 (m, 2H), 2.18 (t, 2H), 2.80 (m, 1H), 6.47 (brd, 1H), 7.31 (m, 5H); MS (HR-FAB) m/z 421.3253 (M+H calc'd for $C_{24}H_{44}N_2O_2Si$ 421.3250).

EXAMPLE 61

[R-(R*,S*)]-N-[2-Amino-1-[[[(1,1-dimethylethyl)dimethylsilyl]oxy]methyl]propyl]-Heptanamide (25c)

A mixture of 28c (208.6 g, 0.50 mmol) and 104 mg of Pd(OH)$_2$ in 15 mL of methyl alcohol is shaken in a Parr apparatus under hydrogen pressure for 18 h. The reaction mixture is filtered through diatomaceous earth and the filtrate concentrated to give 169 mg of the desired product 25c as an oil. NMR $\delta$0.84 (s, 9H), 1.05 (d, 3H), 1.60 (m, 2H), 2.10 (t, 2H), 3.31 (m, 1H), 6.47 (br d, 1H).

EXAMPLE 62

[R-(R*,R*)]-N-[2-Amino-1-[[[(1,1-dimethylethyl)dimethylsilyl]oxy]methyl]propyl]-Heptanamide (25c)

Compound 25d is prepared from 28d, following the procedure used to prepare 25c.

EXAMPLE 63

[S-(R*,S*)]-3-[[(1,1-Dimethylethyl)dimethylsilyl]oxy]-1-methyl-2-[(1-oxoheptyl)aminopropyl]Phenyl Methyl Ester Carbamic Acid (26c)

To a solution of 25c (164 mg, 0.496 mmol) in 1 mL of methylene chloride at 0° C. under argon is added triethylamine (201 mg, 276.5 $\mu$l, 1.98 mmol) followed by the dropwise addition of benzyl chloroformate (169 mg, 142 $\mu$l, 0.992 mmol). The reaction mixture is allowed to warm to room temperature then stirred for 18 h. The reaction mixture is diluted with methylene chloride and water added. The organic layer is separated, washed with brine, dried and concentrated to give 230 mg of a residual pale yellow oil. The residue is purified by chromatography using 1:5 ethyl acetate/hexane to give 92 mg of the desired product 26c. NMR $\delta$0.90 (s, 9H), 1.21 (d, 3H), 1.56 (m, 2H), 2.09 (t, 2H), 3.69 (2dd, 2H), 3.84 (m, 1H), 3.93 (m, 1H), 5.07 (q, 2H), 5.17 (d, 1H), 6.15 (br d, 1H), 7.34 (m, 5H), MS (FAB): m/z 465 (M+H calc'd for $C_{25}H_{45}N_2O_4Si$ 465).

EXAMPLE 64

[R-(R*,R*)]-[3-[[(1,1-Dimethylethyl)dimethylsilyl]oxy]-1-methyl-2-[(1-oxoheptyl)aminopropyl]Phenyl Methyl Ester Carbamic Acid (26d)

Compound 25d is protected according to the procedure used to prepare 26c, giving 26d.

EXAMPLE 65

[S-(R*,S*)]-3-Hydroxy-1-methyl-2-[(1-oxoheptyl)amino]propyl]-Carbamic Acid Phenylmethyl Ester (29c)

Compound 26c is desilylated according to the method in Example 47 to get 29c.

EXAMPLE 66

[R-(R*,R*)]-[3-Hydroxy-1-methyl-2-[(1-oxoheptyl-)amino]propyl]-Carbamic Acid Phenylmethyl Ester (29d)

Compound 26d is desilylated as in Example 65, to get 29d.

EXAMPLE 67

[S-(R*,S*)]-2-[(1-Oxoheptyl)amino1-3-[(phenylmethoxy)carbonyl]amino]-Butanoic Acid (30c)

Oxidation of compound 29c according to the method of Example 49 gives 30c.

EXAMPLE 68

[R-(R*,R*)]-2-[(1-Oxoheptyl)amino]-3-[(phenylmethoxy)carbony]amino]-Butanoic Acid (30d)

Compound 29d is converted to 30d according to Example 67.

EXAMPLE 69

[R-(R*,S*)]-3-Amino-2-[(1-oxoheptyl)amino]Butanoic Acid (2g-2)

Hydrogenolysis of 30c according to Example 28 provides compound 2g-2.

EXAMPLE 70

[R-(R*,R*))-3-Amino-2-[(1-oxoheptyl)amino]Butanoic Acid (2g-3)

Compound 30d is converted to 2o-3 according to Example 69.

EXAMPLE 71

[R-(R*,S*)]-3-Amino-2-[(1-oxoheptyl)amino]Butanoic Acid Methyl Ester

Esterification of 2g-2 according to Example 55, using MeOH as the alcohol, provides 2h-2 as its hydrochloride salt.

EXAMPLE 72

[R-(R*,R*)]-3-Amino-2-(1-oxoheptyl)amino]Butanoic Acid Methyl Ester (2h-3)

Compound 2g-3 is esterified as in Example 71 to get 2h-3 as its hydrochloride salt.

EXAMPLE 73

(S)-5-oxo-3-[(phenylmethoxy)carbonyl]-4-Oxazolidineorooanoic Acid (43c)

A mixture of 100 g (355 mmol) of N-benzyloxycarbonyl-L-Glu (42c) and 213 g of paraformaldehyde is heated to reflux in toluene (1 L). After 4 h the resulting solution is cooled to room temperature and extracted with saturated sodium bicarbonate solution (5×150 mL). The aqueous layers are combined, then partitioned with 400 mL of ethyl acetate and acidified with solid sodium bisulfate. The layers are separated and the organic layer is dried over magnesium sulfate then concentrated to give 89.72 g of the crude acid as a viscous yellow oil: NMR δ7.38 (m, 5H), 5.6 (brs, 1H), 5.21 (d, J=4.7 Hz, 1H), 5.19 (s, 2H), 4.41 (t, J=6 Hz, 1H), 2.6–2.1 (m, 4H).

EXAMPLE 74

(S)-5-oxo-3-(phenylmethoxy)carbonyl]-4-Oxazolidinepropanal (44c)

A solution of 27 g (92.7 mmol) of the crude acid (43c) in 200 mL of THF is cooled to 0° C. and 13 mL (10.7 g, 141 mmol) of borane-methyl sulfide complex is added dropwise via an addition funnel. The reaction is allowed to warm gradually to room temperature and o stirred for 12 h. The resulting mixture is concentrated in vacuo to give a white glassy material which is taken up in 500 mL of methylene chloride and treated with of pyridinium chlorochromate (61 g, 281 mmol) at 0° C. in the presence of 3_molecular sieve. The mixture is allowed to warm to room temperature and stirred for 3 h. The mixture is filtered through diatomaceous earth with ether (200 mL) then concentrated. The residue is taken up in ether and filtered again through diatomaceous earth with ether then concentrated to give 13.22 g of the crude aldehyde as a light green oil: NMR δ9.80 (br s, 1H), 7.40 (m, 5H), 5.55 (br s, 1H), 5.20 (m, 3H), 4.38 (t, J=6.0 Hz, 1H), 2.6–2.1 (m, 4H).

EXAMPLE 75

4-[4-[[(1,1-dimethylethoxy)carbonyl]amino]-5-methoxy-5-oxo-3-pentenyl]-5-oxo-3-oxazolidine-Carboxylic Acid Phenylmethyl Ester (46c)

To a solution of 15.1 g of phosphonate 45 in 300 mL of methylene chloride at −78° C. is added dropwise 102 ml of 0.5 M potassium hexamethyldisilylamid THF solution. The reaction mixture is stirred for 10 minutes and 18 g of crude aldehyde in 30 mL of methylene chloride is added to the enolate solution. The mixture is stirred for 3 h while warming to room temperature. The reaction mixture is quenched with 100 mL of water and extracted with 2×300 mL of ether. The organic extracts are combined and washed with 200 mL of water and 50 mL of brine. After drying over magnesium sulfate, the volume is reduced. The residue is chromatographed using variable gradient hexane/ethyl acetate. The E isomer (2.4 g) elutes first followed by 15.4 g of the desired Z isomer 46c. NMR δ1.45(s, 9H); 2.00–2.40(M, 4H); 3.74(s, 3H); 4.36(b t, 1H); 5.20(M, 4H); 5.54(b s, 1H); 6.43(b t, 1H); 7.37(m, 5H). IR(-neat)cm$^{-1}$: 3350(s), 1800(s), 1740(s); MS(CI): m/z 466(M+NH$_4$); 410(M-C$_4$H$_8$)+; 349 (M-C$_4$H$_8$CO$_2$+H)+; [α]$_D^{26}$ +68±1.

EXAMPLE 76

(Z)-N-[5,6-Didehydro-N$^6$-[(1,1-dimethylethoxy)carbonyl]-6-(methoxycarbonyl)-N$^2$-[(phenylmethoxy)carbonyl]-L-lysyl]-D-alanine Methyl Ester (47c)

A mixture of 3.3 g of D-alanine methyl ester and 7.1 g of 46c is heated at 140° C. for 10 min, then another 1.6 g of D-alanine methyl ester is added. Heating is continued at 140° C. for an additional 10 min. After cooling to ambient temperature the crude product is chromatographed on silica gel using variable gradient hexane/ethyl acetate. Purified product (6.7 g) is recovered. The material is crystallized from hexanes-ether to give 5.8 g of the desired product 47c as a solid. NMR δ1.43(s,d,12H); 1.80–2.10(m,2H); 2.23–2.36(m,2H); 3.72(s,3H); 3.76( s,3H); 4.15–4.27(m,1H); 4.50–4.60(m,1H); 5.11(b s,2H); 5.76(b s,1H); 6.38(b s,1H); 6.47(b t,1H); 6.81(b s,1H); 7.34(m,5H); $^{13}$C-NMR: 17.82(—CH<u>C</u>H$_3$; 24.33(—<u>C</u> H$_2$—CH$_2$); 28.02(C(<u>C</u>H$_3$)$_3$);

30.99(—CH$_2$CH=C); 47.94(—CHCH$_3$); 52.17(—OCH$_3$); 52.29(—OCH$_3$); 54.28(OCCHNH); 66.93(—CH$_2$Ar); 80.43(—OC(CH$_3$)$_3$); 126.57(—HNC=C); 127.86(phenyl ring carbon); 127.94 (phenyl ring carbon); 128.12(phenyl ring carbon); 128.28(phenyl ring carbon); 135.98(phenyl ring carbon); 153.45(OCONH); 156.21(OCONH—); 165.13(—CONH—); 171.04(—CO$_2$—); 172.99(—CO$_2$—). IR(KBr, cm$^{-1}$) 3300(s); 1720(s); 1690(s); 1650(s); 1510(s); MS(CI) m/z 522(MH)$^+$; 466(MH—C$_4$H$_8$)$^+$; 422(MH—C$_4$H$_8$CO$_2$)$^+$. MS(FAB) m/z 544(M+Na)$^+$; 522(MH)$^+$; 466(MH—C$_4$H$_8$)$^+$; Anal Calcd: C, 57.57; H, 6.76; N, 8.06; Found: C, 56.98;H, 6.66; N, 7.88. [α]$_D^{26}$ −7±1; m.p. 120°-121° C.

EXAMPLE 77

N-[N$^6$-[(1,1-Dimethylethoxy)carbonyl]-(R)-6-(methoxycarbonyl)-N$^2$-[(phenylmethoxy)carbonyl]-L-lysyl]-D-Alanine Methyl Ester (40c)

A solution of 8.5 g of 47c in 25 mL of acetic acid and 250 mL of THF is hydrogenated at 48 psi of hydrogen over 0.5 g of (bicyclo(2.2.1.)hepta-2,5-diene[ 2S,3S]bis(-diphenylphosphino)butane)rhodium(I) perchlorate for 18 h. The reaction is filtered and evaporated to a residue. The residue is chromatographed using variable gradient hexane-ethyl acetate to give 7.9 g of reduced product as a residue. Multiple crystallizations give 2.6 g of diastereomerically pure 40c. NMR(CDCl$_3$) δ1.40(d,J=6 Hz,3H); 1.43(s,9H); 1.60-1.97(m,6H); 3.73(s,3H); 3.74(s,3H); 4.12-4.37(m,2H); 4.52-4.61(m,1H); 5.12(bs,3H); 5.44-5.55-(b s,1H); 6.73(b s,1H); 7.36(b s,5H); $^{13}$C-NMR: δ18.02(CH—CH$_3$); 21.12(CH$_2$—CH$_2$—CH$_2$); 28.23(—OC(CH$_3$)$_3$); 31.87(—CH$_2$—CH$_2$); 32.29(—CH$_2$CH$_2$—); 47.99(—CHCH$_3$); 52.23(—OCH$_3$); 52.38(—OCH$_3$); 52.75(OCCHN); 54.41(OCCHN); 67.01(—OCH$_2$Ar); 79.97(—OC(CH$_3$)$_3$); 127.99 (phenyl ring carbon); 128.09 (phenyl ring carbon); 128.44(ArCH); 136.13(ArCC); 155.48(OCONH); 156.23(OCONH); 171.10(—CONH—); 173.03(—CO$_2$—2X); IR(KBr)(cm$^{-1}$): 3340(s); 1760(s); 1740(s); 1680(s); 1660(s); 1660(s); 1520(s); MS(FAB) m/z 546(M+Na)$^+$; 524(MH)$^+$; 424(MH—C$_4$H$_8$CO$_2$)$^+$; Anal. Calcd: C, 57.35;H, 7.12; N, 8.03; Found: C, 57.23;H, 7.27; N, 8.03; rotation [α]$_D^{25}$ −9±1; m.p. 120°-121° C.

EXAMPLE 78

N-[N$^6$-[(1,1-Dimethylethoxy)carbonyl]-R-6-(methoxycarbonyl)-L-Lysyl]-D-Alanine Methyl Ester (3c)

A solution of 40c (248 mg, 0.47 mmol) in methanol (8 mL) is hydrogenated over Pd(OH)$_2$ according to Example 28. After 3 hours, filtration and evaporation gives a colorless glass. NMR(CDCl$_3$) δ3.50(m,1H), 3.80(s,6H), 4.30(m,1H), 4.55(m,1H), 5.15(d,1H), 7.85(br s,1H).

EXAMPLE 79

N-[N$^6$-[1,1-dimethylethoxy)carbonyl]-6-(methoxycarbonyl)-N$^2$-[[[3-oxo-2-[(1-oxoheptyl)amino]-3-(phenylmethoxy)propyl]amino]carbonyl]-L-lysyl]-D-alanine (1b-1)

A solution of 30 (94.5 mg, 0.24 mmol) in dried THF (3A sieve 0.8 mL) is added dropwise under argon to a mixture of 1,1'-carbonyldiimidazole (39.34 mg, 0.24 mmol, dried over P in 1.8 mL dried THF. The mixture is stirred for 2 h and 2h-1(83.3 mg, 0.24 mmol) and TEA (34 ul, 0.24 mm) are added. The resulting mixture is stirred for 18 h at ambient temperature. The mixture is diluted with water and extracted with ethyl acetate. The organic layer is separated, washed with brine, dried, filtered and evaporated to a residue. The residue is purified by chromatography by elution with 1-2% methanol in chloroform giving 109.3 mg of 1b-1 as an off white solid. NMR δ0.88(t,3H), 2.22(t,2H) 3.59(m,2H), 3.70(s,3H), 3.73(s,3H), 4.26(m,1H), 4.52(t,1H), 4.63(m,1H), 5.32(d,2H), 5.63(d,1H), 7.07(d,1H), 7.20(d,1H); MS(HR-FAB) m/z 722.3980(M+H, calcd for C$_{35}$H$_{56}$N$_5$O$_{11}$ 722.3976).

EXAMPLE 80

N-[6-(methoxycarbonyl)-N$^2$-[[[3-oxo-2-1-oxo-heptyl)amino]-3-(phenylmethoxy)propyl]amino]carbonyl]-L-lysyl]-D-alanine methyl ester (1b-2)

To 16 mg of 1b-1 under argon at 0° C. is added 100 μl of TFA followed by stirring for 1 h. The volatiles are evaporated to give 11.1 mg of 1b-2. NMR(CD$_3$OD) δ0.80(t,3H), 1.30(d,3H), 2.15(t,2H), 3.32(m,1H), 3.56(m,1H), 3.60(s,3H), 3.73(s,3H), 3.95(m,1H), 4.15(m,1H), 4.30(q,1H), 4.38(m,1H), 5.07(d,2H), 7.28(m,5H); MS(HR-FAB) m/z 622.3435 (M+H, calcd for C$_{30}$H$_{48}$N$_5$O$_9$ 622.3452).

EXAMPLE 81

N-N$^2$-[[[2-carboxy-2-[(1-oxoheptyl)amino]ethyl]amino]carbonyl]-N$^6$-[(1,1-dimethylethoxy)carbonyl]-6-(methoxy carbonyl)-L-lysyl-D-alanine methyl ester (1b-3)

To 70 mg of 1b-1 in 7 mL of methyl alcohol is added 31 mg of Pd(OH)2 on carbon and the reaction mixture hydrogenated for 4 h according to Example 28. The reaction mixture is filtered through a pad of diatomaceous earth. The filtrate is concentrated to give 53.8 mg of 1b-3 as a glass. NMR(CD$_3$OD) δ0.80(t,3H), 2.15(t,2H), 3.32(m,1H), 3.56(m,1H), 3.60(s,6H), 3.95(m,1H), 4.15(m,1H), 4.30(q,1H), 4.38(m,1H); MS(HR-FAB) m/z 632.3493 (M+H, calcd for C$_{28}$H$_{50}$N$_5$O$_{11}$ 632.3506).

EXAMPLE 82

N-[N$^2$-[[[2-carboxy-2-[(1-oxoheptyl)aminolethyl]amino]carbonyl]-6-(methoxycarbonyl)-L-lysyl-D-alanine methyl ester (1b-4).

To 40.2 mg of 1b-3 under argon at 0° C. is added 300 μl of TFA following the procedure of Example 80. The volatiles are evaporated and the concentrate dried overnight to give 47 mg of 1b-4. NMR(CD$_3$OD) δ0.80(t,3H), 1.30(d,3H), 2.15(t,2H), 3.28(m,1H), 3.56(m,1H), 3.62(s,3H), 3.75(s,3H), 3.95(m,1H), 4.13(m,1H), 4.31(q,1H), 4.43(m,1H); MS(HR-FAB) m/z 532.2972 (M+H, calcd for C$_{23}$H$_{42}$N$_5$O$_9$ 532.2983).

EXAMPLE 83

N-[6-carboxy-N$^2$-[[[carboxy-2-[(1-oxoheptyl)amino]ethyl]amino]carbonyl]-N$^6$-[(1,1-dimethylethoxy)carbonyl]-L-lysyl-D-alanine (1b-5)

To a solution of 135.9 mg of 1b-1 in 2.7 mL of methyl alcohol is added 104 mg of potassium carbonate and 0.9 mL of water followed by stirring at room temperature for 20 hours. The reaction mixture is evaporated to a residue which is dissolved in 1 mL of water and acidified with 1N HCl to pH 2. The reaction mixture is stirred for 5 minutes and extracted 2× with ethyl acetate. The combined organic extracts are washed with brine, dried and evaporated to give 106 mg of residue.

The residue is triturated with 3×5 ml of ether and the ether decanted. The solid residue is dried to give 91.7 mg of product 1b-5 as a white solid. NMR(CD$_3$OD) $\delta$0.80(t,3H), 2.15(t,2H), 3.32(m,1H), 3.56(m,1H), 3.95(s,3H), 4.15(m,1H), 4.30(q,1H), 4.38(m,1H); MS(HR-FAB) m/z 604.3200 (M+H, calcd for C$_{26}$H$_{46}$N$_5$O$_{11}$ 604.3194).

EXAMPLE 84

N-6-carboxy-N$^2$-[[[2-carboxy-2-[(1-oxoheptyl)amino]ethyl]amino]carbonyl]-L-lysyl]-D-alanine (1b-11)

To 85.9 mg of 1b-5 under argon is treated with 500 $\mu$l of TFA according to Example 80. The volatiles are evaporated to a residue which is triturated with ether 3× and the ether is decanted. The residue is dried to give 77.9 mg of 1b-11 as a white solid. NMR(CD$_3$OD) $\delta$0.80(t,3H), 2.16(t,2H), 3.22(br s,5H), 3.58(m,2H), 3.85(m,1H), 4.15(m,1H), 4.30(d,1H), 4.40(m,1H); MS(HR-FAB) m/z 526.2482 (M+H, calcd for C$_{21}$H$_{38}$N$_5$O$_9$ 526.2489).

EXAMPLE 85

[S-(R*,S*)]-N-N$^6$-[(1,1-Dimethylethoxy)carbonyl-N$^2$-[[[3-methoxy-1-methyl-3-oxo-2-[(1-oxoheptyl)amino]-propyl]amino]carbonyl]-(R)-6-(methoxycarbonyl)-L-lysyl]-D-Alanine (1b-6)

Amine 2h-2 is coupled with amine 3c according to the procedure described in Example 79. The urea is purified by chromatography and identified as 1b-6.

EXAMPLE 86

[R-(R*,R*)]-N[N$^6$-[(1,1-Dimethylethoxy)carbonyl]-N$^2$-[[3-methoxy-1-methyl-3-oxo-2-(1-oxoheptyl)amino]-propyl]aminocarbonyl](R)-6-(methoxycarbonyl)-L-lysyl]-D-Alanine Methyl Ester (1b-7)

Amine 2h-3 is converted to urea 1b-7 according to Example 85.

EXAMPLE 87

[S-(R*,S*)]-N-(R)-6-carboxy-N$^2$-[[[2-carboxy-1-methyl-2-[(1-oxoheptyl)amino]ethyl]amino]carbonyl]-N$^6$-[(1,1-dimethylethoxy)carbonyl]-L-lysyl]-D-Alanine (1b-8)

Hydrolysis of 1b-6 according to the procedure in Example 83, provides 1b-8.

EXAMPLE 88

[R-(R*,R*)]-N-(R)-6-Carboxy-N$^2$-[[[2-carboxy-1-methyl-2-(1-oxoheptyl)amino]ethyl]amino]carbonyl]-N$^6$-[(1,1-dimethylethoxy)carbonyl]-L-lysyl]-D-Alanine (1b-9)

Hydrolysis of 1b-7 according to Example 87 provides 1b-9.

EXAMPLE 89

[S-(R*,S*)]-N-(R)-6-carboxy-N$^2$-[[[2-carboxy-1-methyl-2-[(1-oxoheptyl)amino]ethyl]amino]carbonyl]-L-lysyl]-D-Alanine (1b-12)

Deblocking of the amine group of 1b-8 with TFA, according to the procedure in Example 84, provides 1b-12.

EXAMPLE 90

[R-(R*,R*)]-N-(R)-6-carboxy-N$^2$-[[[2-carboxy-1-methyl-2-[(1-oxoheptyl)amino]ethyl]amino]carbonyl]-L-lysyl]-D-Alanine (1b-13)

Compound 1b-9 is deprotected according to the procedure in Example 89, to get 1b-13.

We claim:
1. A compound of the Formula I:

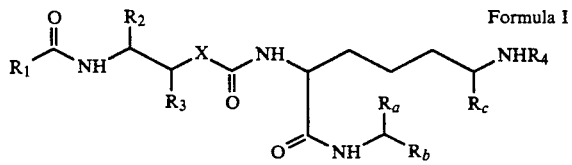

wherein:
R$_1$ is selected from the group consisting of hydrogen, a substituted or unsubstituted (C$_1$-C$_{20}$) alkyl group, a substituted or unsubstituted cycloalkyl group, a substituted or unsubstituted cycloalkylalkyl group, a vinyl group, an acetylene group, a substituted or unsubstituted amino group, a substituted or unsubstituted acylamino group, a substituted or unsubstituted aryl group, a substituted or unsubstituted aralkyl group, a substituted or unsubstituted aryloxy group, a substituted or unsubstituted alkoxyaryl group, a substituted or unsubstituted alkoxyaralkyl group and a substituted or unsubstituted monocyclic or bicyclic heterocyclic group containing from 1 to 4 hetero atoms selected from the group consisting of nitrogen, sulfur and oxygen atoms; R$_a$ and R$_3$ are independently selected from hydrogen, substituted or unsubstituted (C$_1$-C$_6$) alkyl, substituted or unsubstituted alkoxyalkyl, substituted or unsubstituted cycloalkyl, substituted or unsubstituted cycloalkylalkyl, substituted or unsubstituted aryl, substituted or unsubstituted aralkyl, substituted or unsubstituted alkoxyaralkyl, vinyl, acetylene and a sustituted or unsubstituted monocyclic or bicyclic heterocycle containing from 1 to 4 heteroatoms selected from the group consisting of nitrogen, sulfur and oxygen atoms provided that, in the case of R3, the hetero atoms in said heterocycle are not directly bonded to the —CH— group of the —CH—X— moiety; and R$_2$, R$_b$ and R$_c$ are independently selected from carboxy or protected carboxy, carboxy or protected carboxyloweralkyl and carboxyamide;

X is oxygen or nitrogen; and

R$_4$ is H or an amino protecting group; wherein the substituents in the aforementioned substituted alkyl, cycloalkyl, cycloalkylalkyl, amino, acylamino, aryl, aralkyl, aryloxy, alkoxyaryl, alkoxyaralkyl and heterocyclic groups are selected from the group consisting of halogen, hydroxyl, lower alkyl, lower alkoxy, aryloxy, aralkyloxy, amino, monoor di-lower alkylamino, arylamino, aralkylamino, carboxyl, formyl, lower alkoxycarbonyl, aryloxycarbonyl, aralkyloxycarbonyl, lower alkylthio, arylthio, aralkylthio, arylsulfinyl, arylsulfinyl, aralkylsulfinyl, lower alkylsulfonyl, arylsulfonyl, aralkylsulfonyl and a monocyclic or bicyclic heterocyclic group having 1-4 hetero atoms selected from nitrogen, sulfur and oxygen;

and the pharmaceutically acceptable salts thereof.

2. A compound according to claim 1 having the formula:

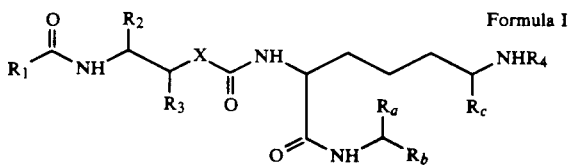

wherein:
- $R_1$ is selected from the group consisting of a substituted or unsubstituted ($C_1$-$C_{20}$) alkyl group, a substituted or unsubstituted cycloalkyl group, a substituted or unsubstituted cycloalkylalkyl group, a substituted or unsubstituted aryl group, a substituted or unsubstituted aralkyl group, a substituted or unsubstituted aryloxy group, a substituted or unsubstituted alkoxyaryl group, and a substituted or unsubstituted alkoxyaralkyl group Wherein the aryl moiety in the foregoing groups is selected from substituted or unsubstituted phenyl,;
- $R_a$ and $R_3$ are independently selected from hydrogen, and substituted or unsubstituted ($C_1$-$C_6$) alkyl;
- $R_2$, and $R_c$ are independently selected from carboxy or protected carboxy, carboxy or protected carboxyloweralkyl and carboxyamide;
- X is oxygen or nitrogen; and
- $R_4$ is H or an amino protecting group;

wherein the substituents in the aforementioned substituted alkyl, cycloalkyl, cycloalkylalkyl, aryl, aralkyl, aryloxy, alkoxyaryl or alkoxyaralkyl are selected from halogen, hydroxyl, lower alkyl, lower alkoxy, aryloxy, aralkyloxy, amino, mono- or di-lower alkylamino, arylamino, aralkylamino, carboxyl, formyl, lower alkoxy- carbonyl, aryloxycarbonyl, aralkyloxycarbonyl, lower alkylthio, arylthio, aralkylthio, arylsulfinyl, aralkylsulfinyl, lower alkylsulfonyl, arylsulfonyl, aralkylsulfonyl and a monocyclic or bicyclic heterocyclic group having 1-4 hetero atoms selected from nitrogen, sulfur and oxygen.

3. A compound according to claim 1 having the formula:

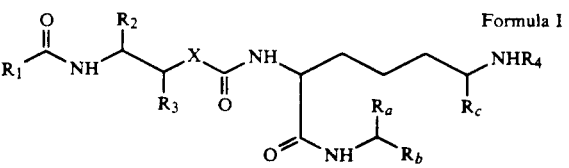

wherein:
- $R_1$ is selected from the group consisting of a ($C_4$-$C_{14}$) alkyl group, a cycloalkyl group, a ($C_2$-$C_8$) alkyl substituted cycloalkyl group, a phenyl group, a benzyl group, a ($C_4$-$C_8$) alkylphenyl group, and a ($C_1$-$C_6$) alkylalkoxyphenylmethyl group;
- $R_a$ and $R_3$ are independently selected from hydrogen and ($C_1$-$C_6$) alkyl;
- $R_2$, $R_b$ and $R_c$ are independently selected from carboxy or protected carboxy, carboxy or protected carboxyloweralkyl and carboxyamide;
- X is oxygen or nitrogen; and
- $R_4$ is H or an amino protecting group.

4. A compound according to claim 1 having the formula:

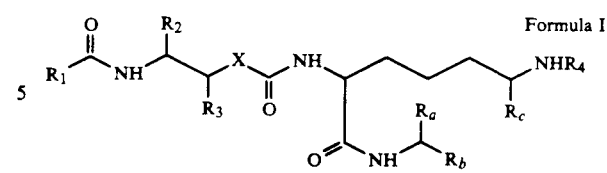

- $R_1$ is selected from the group consisting of an n-hexyl group, a 4-n-pentylcyclohexyl group;
- $R_a$ and $R_3$ are independently selected from hydrogen and methyl;
- $R_2$, $R_b$ and $R_c$ are carboxy;
- X is oxygen or nitrogen; and
- $R_4$ is H.

5. A compound according to claim 1 having the formula:

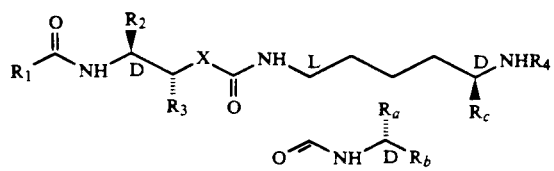

wherein:
- $R_1$ is selected from the group consisting of hydrogen, a substituted or unsubstituted ($C_1$-$C_{20}$) alkyl group, a substituted or unsubstituted cycloalkyl group, a substituted or unsubstituted cycloalkylalkyl group, a vinyl group, an acetylene group, a substituted or unsubstituted amino group, a substituted or unsubstituted acylamino group, a substituted or unsubstituted aryl group, a substituted or unsubstituted aralkyl group, a substituted or unsubstituted aryloxy or alkoxyaryl group, or alkoxyaralkyl or a substituted or unsubstituted monocyclic or bicyclic heterocyclic group containing from 1 to 4 hetero atoms selected from the group consisting of nitrogen, sulfur and oxygen atoms;
- $R_a$ and $R_3$ are independently selected from hydrogen, substituted or unsubstituted ($C_1$-C alkyl, substituted or unsubstituted alkoxyalkyl, substituted or unsubstituted cycloalkyl, substituted or unsubstituted cycloalkylalkyl, substituted or unsubstituted aryl, substituted or unsubstituted aralkyl, substituted or unsubstituted alkoxyaralkyl, vinyl, acetylene and a sustituted or unsubstituted monocyclic or bicyclic heterocycle containing from 1 to 4 heteroatoms selected from the group consisting of nitrogen, sulfur and oxygen atoms provided that, in the case of $R_3$, the hetero atoms in said heterocycle are not directly bonded to the —CH— group of the —CH—X— moiety; and
- $R_2$, $R_b$ and $R_c$ are independently selected from carboxy or protected carboxy, carboxy or protected carboxyloweralkyl and carboxyamide;
- X is oxygen or nitrogen; and
- $R_4$ is H or an amino protecting group; wherein the substituents for the aforementioned substituted groups are as defined in claim 1.

6. A compound according to claim 1 having the formula:

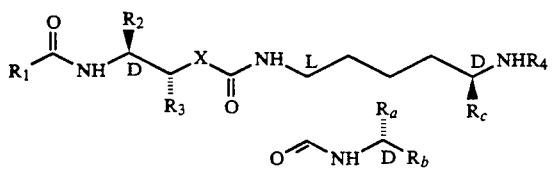

wherein:
- R₁ is selected from the group consisting of a substituted or unsubstituted ($C_1$–$C_{20}$) alkyl group, a substituted or unsubstituted cycloalkyl group, a substituted or unsubstituted cycloalkylalkyl group, a substituted or unsubstituted aryl group, a substituted or unsubstituted aralkyl group, a substituted or unsubstituted aryloxy group, a substituted or unsubstituted alkoxyaryl group, and a substituted or unsubstituted alkoxyaralkyl group wherein the aryl moiety in the foregoing groups is selected from substituted or unsubstituted phenyl;
- $R_a$ and $R_3$ are independently selected from hydrogen, and substituted or unsubstituted ($C_1$–$C_6$) alkyl;
- $R_2$, $R_b$ and $R_c$ are independently selected from carboxy or protected carboxy, carboxy or protected carboxyloweralkyl and carboxyamide;
- X is oxygen or nitrogen;
- $R_4$ is H or an amino protecting group;
wherein the substituents in the aforementioned substituted groups are as defined in claim 1.

7. A compound according to claim 1 having the formula:

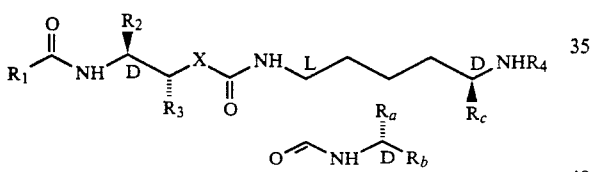

wherein:
- R₁ is selected from the group consisting of a ($C_4$–$C_{14}$) alkyl group, a cycloalkyl group, a ($C_2$–$C_8$) alkyl substituted cycloalkyl group, a phenyl group, benzyl group, a ($C_4$–$C_8$) alkylphenyl group, and a ($C_1$–$C_6$) alkylalkoxyphenylmethyl group;
- $R_a$ and $R_3$ are independently selected from hydrogen, and ($C_1$–$C_6$) alkyl;
- $R_2$, $R_b$ and $R_c$ are independently selected from carboxy or protected carboxy, carboxy or protected carboxyloweralkyl and carboxyamide;
- X is oxygen or nitrogen; and
- $R_4$ is H or an amino protecting group.

8. A compound according to claim 1 having the formula:

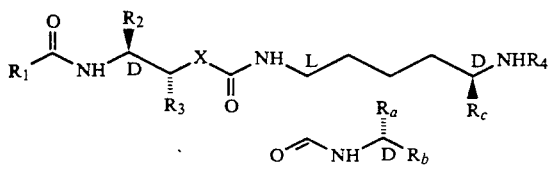

R₁ is selected from the group consisting of an n-hexyl group, a 4-n-pentylcyclohexyl group;
$R_a$ and $R_3$ are independently selected from hydrogen or methyl;

$R_2$, $R_b$ and $R_c$ are carboxy;
X is oxygen or nitrogen; and
$R_4$ is H.

9. A compound according to claim 1 having the formula:

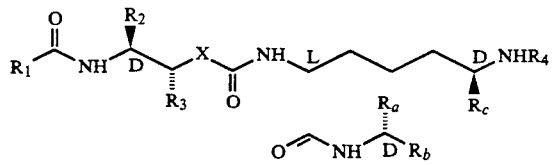

wherein:
- R₁ is selected from the group consisting of an n-hexyl group, a 4-n-pentylcyclohexyl group;
- $R_a$ and $R_3$ are independently selected from hydrogen or methyl;
- $R_2$, $R_b$ and $R_c$ are carboxy;
- X is oxygen; and
- $R_4$ is H.

10. A compound according to claim 1 having the formula:

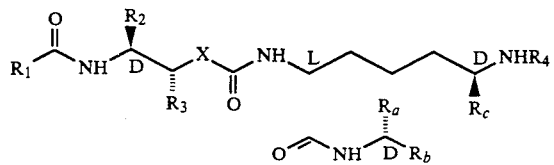

wherein:
- R₁ is an n-hexyl group;
- $R_a$ and $R_3$ are methyl;
- $R_2$, $R_b$ and $R_c$ are carboxy;
- X is oxygen; and
- $R_4$ is H.

11. The compound according to claim 1 [S-(R*,S*)]-N-[(R)-6-carboxy-N²-[[2-carboxy-1-methyl-2-[(1-oxoheptyl)amino]ethoxy]carbonyl]-L-lysyl]-D-Alanine.

12. The compound according to claim 1 [S-(R*,R*)]-N-[(R)-6-carboxy-N²-[[2-carboxy-1-methyl-2-[(1-oxoheptyl)amino]ethoxy]carbonyl]-L-lysyl]-D-Alanine.

13. The compound according to claim 1 [R-(R*,S*)]-N-[(R)-6-carboxy-N²-[[2-carboxy-1-methyl-2-[(1-oxoheptyl)amino]ethoxy]carbonyl]-L-lysyl]-D-Alanine.

14. The compound according to claim 1 (R)-N-[(R)-6-carboxy-N²-[[2-carboxy-2-[(1-oxoheptyl) amino]ethoxy]carbonyl]-L-lysyl]-D-Alanine.

15. The compound according to claim 1 [(R)-6-Carboxy-N²-[[2-carboxy-1-methyl-2-[[(4-pentylcyclohexyl)carbonyl]amino]ethoxy]carbonyl]-L-lysyl]-D-Alanine.

16. The compound according to claim 1 N-[N²-[[2-[[(4-Butoxyphenyl)acetyl]amino]-2-carboxy-1-methylethoxy]carbonyl]-(R)-6-carboxy-L-lysyl]-D-Alanine.

17. The compound according to claim 1 [R-(R*,R*)]-N-[(R)-6-carboxy-N²-[[1-[carboxy[(1-oxoheptyl)amino]methyl]propoxy]carbonyl]-L-lysyl]-D-Alanine.

18. The compound according to claim 1 [S-(R*,S*)]-N-[(R)-6-carboxy-N²-[[1-[carboxy[(1-oxoheptyl)amino]methyl]propoxy]carbonyl]-L-lysyl]-D-Alanine.

19. The compound according to claim 1 N-[6-(methoxycarbonyl)-N²-[[[3-oxo-2-[1-oxo-heptyl)amino]-3-

(phenylmethoxy)propyl]amino]carbonyl]-L-lysyl-D-alanine methyl ester.

20. The compound according to claim 1 N-[$N^2$-[[[2-carboxy-2-[(1-oxoheptyl)amino]ethyl]amino]carbonyl]-6-(methoxycarbonyl)-L-lysyl]-D-alanine methyl ester.

21. The compound according to claim 1 N-[6-carboxy-$N^2$-[[[carboxy-2-[(1-oxoheptyl)amino]ethyl]amino]carbonyl]-$N^6$-[(1,1-dimethylethoxy)carbonyl]-L-lysyl-D-alanine.

22. The compound according to claim 1 N-[6-carboxy-$N^2$-[[[2-carboxy-2-[(1-oxoheptyl)amino]ethyl]amino]carbonyl]-L-lysyl]-D-alanine.

23. The compound accordinq to claim 1 [S-(R*,S*)]-N-[(R)-6-carboxy-$N^2$-[[[2-carboxy-1-methyl-2-[(1-oxoheptyl)amino]ethyl]amino]carbonyl]-L-lysyl]-D-Alanine.

24. The compound according to claim 1 [R-(R*,R*)]-N-[(R)-6-carboxy-$N^2$-[[[2-carboxy-1-methyl-2-[(1-oxoheptyl)amino]ethyl]amino]carbonyl]-L-lysyl]-D-Alanine.

25. A pharmaceutical composition useful for inducing the production of growth factors (IL-6 and $CSF^{25}$) which regulate neutrophil production in the bone marrow of a mammal comprising a suitable pharmaceutical carrier and an effective amount of a compound of claim 1.

* * * * *

UNITED STATES PATENT AND TRADEMARK OFFICE
CERTIFICATE OF CORRECTION

PATENT NO. : 5,312,831

DATED : May 17, 1994

INVENTOR(S) : Ayral-Kaloustian, Steven R. Schow, Mila T. Du, James J. Gibbons

It is certified that error appears in the above-indentified patent and that said Letters Patent is hereby corrected as shown below:

Col 6, lines 57-63, delete the following structure

"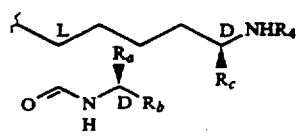"

and insert the following structure therefor:

—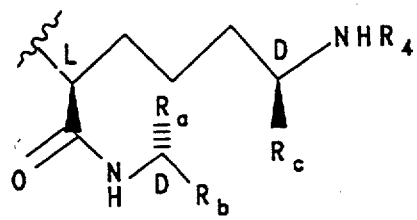—

UNITED STATES PATENT AND TRADEMARK OFFICE
CERTIFICATE OF CORRECTION

PATENT NO. : 5,312,831
DATED : May 17, 1994
INVENTOR(S) : Ayral-Kaloustian, Steven R. Schow, Mila T. Du, James J. Gibbons It is certified that error appears in the above-indentified patent and that said Letters Patent is hereby corrected as shown below:

Col. 7, lines 1-8, delete the following structure

"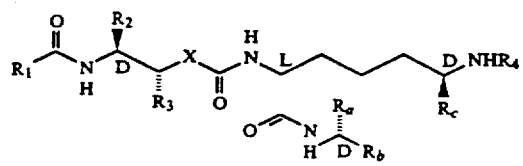"

and insert the following structure therefor:

--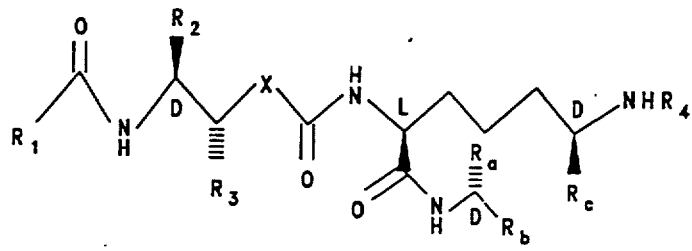--

UNITED STATES PATENT AND TRADEMARK OFFICE
CERTIFICATE OF CORRECTION

PATENT NO. : 5,312,831
DATED : May 17, 1994
INVENTOR(S) : Ayral-Kaloustian, Steven R. Schow, Mila T. Du, James J. Gibbons It is certified that error appears in the above-indentified patent and that said Letters Patent is hereby corrected as shown below:

Col 44, lines 20-28, delete the following structure

"                                                                                    "

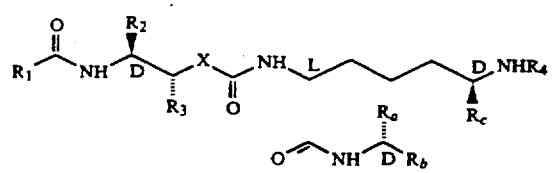

and insert the following structure therefor:

--                                                                                    --

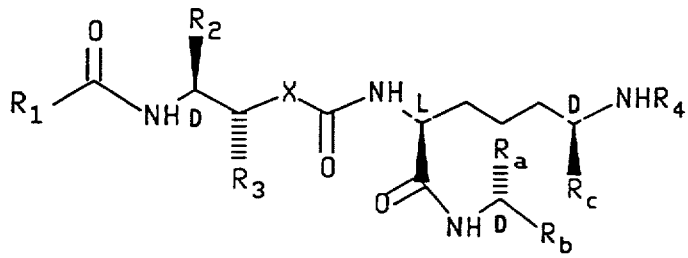

UNITED STATES PATENT AND TRADEMARK OFFICE
CERTIFICATE OF CORRECTION

PATENT NO. : 5,312,831

DATED : May 17, 1994

INVENTOR(S) : Ayral-Kaloustian, Steven R. Schow, Mila T. Du, James J. Gibbons

It is certified that error appears in the above-indentified patent and that said Letters Patent is hereby corrected as shown below:

Col. 45, lines 1-9, delete the following structure

"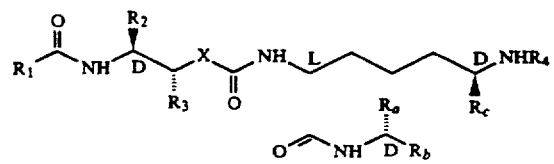"

and insert the following structure therefor:

--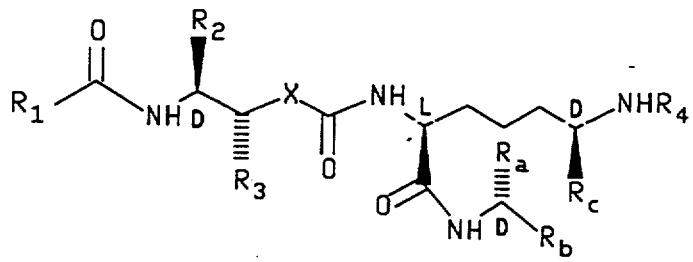--

UNITED STATES PATENT AND TRADEMARK OFFICE
CERTIFICATE OF CORRECTION

PATENT NO. : 5,312,831
DATED : May 17, 1994
INVENTOR(S) : Ayral-Kaloustian, Steven R. Schow, Mila T. Du, James J. Gibbons Page 5 of 9

It is certified that error appears in the above-indentified patent and that said Letters Patent is hereby corrected as shown below:

Col. 45, lines 33-39, delete the following structure

"

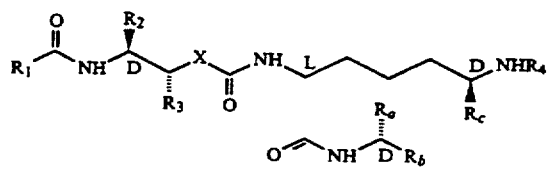

"

and insert the following structure therefor:

--

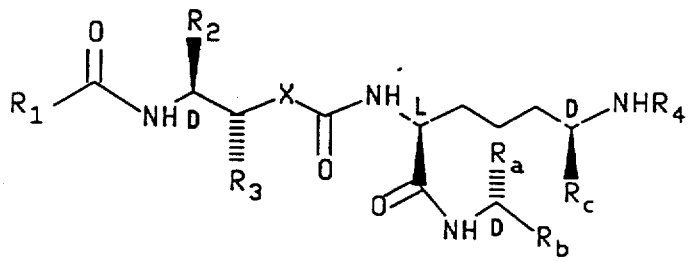

--

UNITED STATES PATENT AND TRADEMARK OFFICE
CERTIFICATE OF CORRECTION

PATENT NO. : 5,312,831  
DATED : May 17, 1994  
INVENTOR(S) : Ayral-Kaloustian, Steven R. Schow, Mila T. Du, James J. Gibbons Page 6 of 9

It is certified that error appears in the above-indentified patent and that said Letters Patent is hereby corrected as shown below:

Col. 45, lines 56-64, delete the structure

"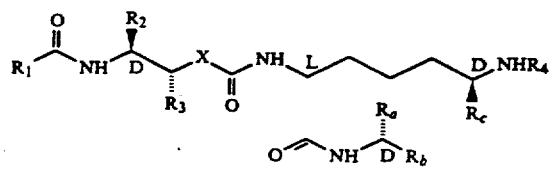"

and insert the following structure therefor:

--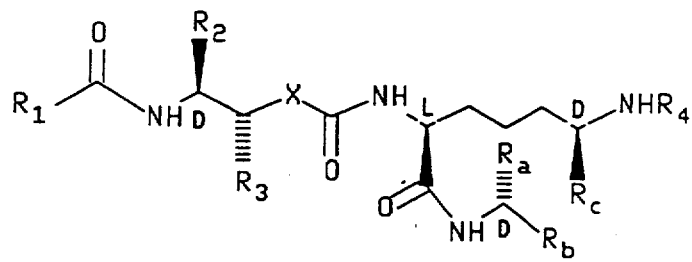--

UNITED STATES PATENT AND TRADEMARK OFFICE
CERTIFICATE OF CORRECTION

PATENT NO. : 5,312,831
DATED : May 17, 1994
INVENTOR(S) : Ayral-Kaloustian, Steven R. Schow, Mila T. Du, James J. Gibbons It is certified that error appears in the above-indentified patent and that said Letters Patent is hereby corrected as shown below:

Col. 46, lines 6-13, delete the structure

"  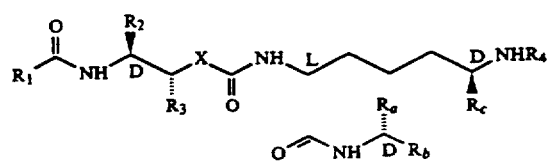  "

and insert the following structure therefor:

--  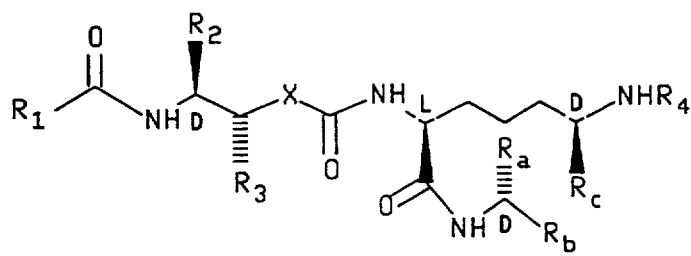  --

UNITED STATES PATENT AND TRADEMARK OFFICE
CERTIFICATE OF CORRECTION

PATENT NO. : 5,312,831

DATED : May 17, 1994

INVENTOR(S) : Ayral-Kaloustian, Steven R. Schow, Mila T. Du, James J. Gibbons

It is certified that error appears in the above-indentified patent and that said Letters Patent is hereby corrected as shown below:

Col. 46, lines 25-32, delete the structure

"
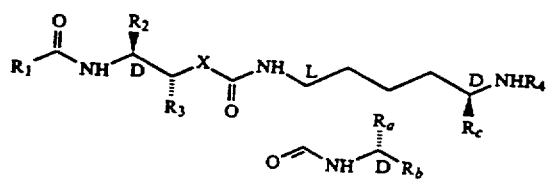
"

UNITED STATES PATENT AND TRADEMARK OFFICE
CERTIFICATE OF CORRECTION

PATENT NO. : 5,312,831
DATED : May 17, 1994
INVENTOR(S) : Ayral-Kaloustian, Steven R. Schow, Mila T. Du, James J. Gibbons It is certified that error appears in the above-indentified patent and that said Letters Patent is hereby corrected as shown below:

and insert the following structure therefor:

--  --

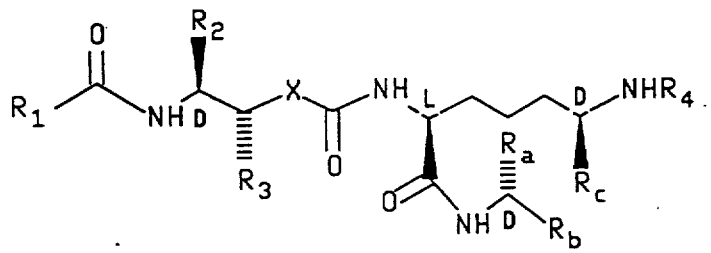

Signed and Sealed this

Fifteenth Day of November, 1994

BRUCE LEHMAN

Attest:

Attesting Officer

Commissioner of Patents and Trademarks